(12) United States Patent
Samangooie

(10) Patent No.: US 11,160,351 B2
(45) Date of Patent: Nov. 2, 2021

(54) HAND-HELD APPLICATOR

(71) Applicant: CASEMED ENGINEERING, LLC, Waukegan (IL)

(72) Inventor: Casey Samangooie, Wadsworth, IL (US)

(73) Assignee: CASEMED ENGINEERING, LLC, Wadsworth, IL (US)

( * ) Notice: Subject to any disclaimer, the term of this patent is extended or adjusted under 35 U.S.C. 154(b) by 0 days.

(21) Appl. No.: 15/753,529

(22) PCT Filed: Feb. 1, 2018

(86) PCT No.: PCT/US2018/016374
§ 371 (c)(1),
(2) Date: Feb. 19, 2018

(87) PCT Pub. No.: WO2019/103755
PCT Pub. Date: May 31, 2019

(65) Prior Publication Data
US 2020/0214423 A1    Jul. 9, 2020

Related U.S. Application Data

(60) Provisional application No. 62/590,606, filed on Nov. 26, 2017.

(51) Int. Cl.
*B43K 5/14* (2006.01)
*A45D 40/24* (2006.01)
(Continued)

(52) U.S. Cl.
CPC .............. *A45D 40/24* (2013.01); *A45D 34/04* (2013.01); *A61M 35/006* (2013.01);
(Continued)

(58) Field of Classification Search
CPC ..... A45D 40/24; A45D 34/04; A61M 35/003; A61M 35/006; B65D 81/3261
(Continued)

(56) References Cited

U.S. PATENT DOCUMENTS 3,116,732 A   1/1964   Cahill
3,386,793 A   6/1968   Stanton
(Continued)

FOREIGN PATENT DOCUMENTS

FR   2995769 A1   3/2014
FR   2995769 B1   1/2016
(Continued)

OTHER PUBLICATIONS

European Search Report, Application No./Patent No. 18880721.8-1005/3713443 PCT/US2018016374, CaseMed Engineering, LLC, dated Aug. 4, 2021.
(Continued)

*Primary Examiner* — Jennifer C Chiang
(74) *Attorney, Agent, or Firm* — Flener IP & Business Law; Zareefa B. Flener

(57) ABSTRACT

A hand-held applicator includes a first applicator layer adjacent a first reservoir and a finger-receiving space for holding the applicator. When the first applicator layer is external facing, the fill material is dispensed outside the applicator and when the first applicator layer faces into the finger receiving space the fill material is dispensed into the finger-receiving space and applied to the finger or fingers in the finger-receiving space. The applicator may further include a second applicator layer adjacent a second reservoir and opposite the first applicator layer and first reservoir to securely store and dispense a second amount of the fill material. Reservoir access layers separate applicator layers and reservoirs, transform between a first, closed position
(Continued)

where the fill material is securely stored in a reservoir and a second, open position where fill material is dispensed from a reservoir through an applicator layer.

37 Claims, 21 Drawing Sheets

(51) Int. Cl.
*A45D 34/04* (2006.01)
*A61F 13/40* (2006.01)
*B65D 81/32* (2006.01)
*A47K 7/03* (2006.01)

(52) U.S. Cl.
CPC .. *B65D 81/3261* (2013.01); *A45D 2200/1018* (2013.01); *A45D 2200/1045* (2013.01); *A47K 7/03* (2013.01); *A61M 2209/088* (2013.01)

(58) Field of Classification Search
USPC .............................................. 401/132, 133, 7
See application file for complete search history.

(56) References Cited

U.S. PATENT DOCUMENTS

| | | | |
|---|---|---|---|
| 3,466,131 A | 9/1969 | Arcudi | |
| 3,986,640 A | 10/1976 | Redmond | |
| 3,998,559 A | 12/1976 | Hoyt | |
| 4,140,409 A | 2/1979 | DeVries | |
| 4,430,013 A | 2/1984 | Kaufman | |
| 4,475,835 A | 10/1984 | Verboom et al. | |
| 4,526,176 A | 7/1985 | Bremer et al. | |
| 4,800,904 A | 1/1989 | Kinseley et al. | |
| 4,893,956 A | 1/1990 | Wojcik et al. | |
| 4,963,045 A | 10/1990 | Willcox | |
| 5,090,832 A | 2/1992 | Rivera et al. | |
| 5,681,574 A | 10/1997 | Haber et al. | |
| 5,775,826 A | 7/1998 | Miller | |
| 6,425,701 B1 | 7/2002 | Jacobs | |
| 6,547,468 B2 | 4/2003 | Gruenbacher et al. | |
| 7,108,440 B1 | 9/2006 | Gruenbacher et al. | |
| 7,255,506 B2 * | 8/2007 | Gruenbacher | A61Q 19/00 401/7 |
| 7,264,414 B2 | 9/2007 | McReynolds et al. | |
| 7,416,358 B2 * | 8/2008 | Legendre | A45D 40/26 401/205 |
| 7,507,047 B2 * | 3/2009 | Oberstadt | A46B 5/04 401/132 |
| 7,575,384 B2 | 8/2009 | Bauer et al. | |
| 7,631,645 B2 | 8/2009 | Gayton et al. | |
| 7,651,290 B2 | 1/2010 | Bauer et al. | |
| 7,674,058 B2 * | 3/2010 | Berger Sharp | A46B 5/04 401/132 |
| 8,157,464 B2 * | 4/2012 | Prax | A45D 34/04 401/132 |
| 8,215,859 B2 | 7/2012 | Kaufman et al. | |
| 8,425,136 B2 | 4/2013 | Littig et al. | |
| 8,534,947 B2 | 9/2013 | Prax | |
| 8,814,455 B2 * | 8/2014 | Golden | A45D 40/0087 401/132 |
| 8,910,830 B2 | 12/2014 | May | |
| 8,926,212 B2 * | 1/2015 | Gundersen | A45D 37/00 401/205 |
| 9,022,679 B2 | 5/2015 | Samangooie | |
| 2002/0032943 A1 | 3/2002 | James et al. | |
| 2002/0197094 A1 | 12/2002 | Gruenbacher et al. | |
| 2004/0109720 A1 | 6/2004 | Gruenbacher et al. | |
| 2005/0284777 A1 | 12/2005 | Wilkman | |
| 2006/0039742 A1 | 2/2006 | Cable, Jr. et al. | |
| 2007/0048063 A1 | 3/2007 | Bauer et al. | |
| 2007/0053737 A1 | 3/2007 | Morris et al. | |
| 2007/0183836 A1 | 8/2007 | Lampe et al. | |
| 2008/0317389 A1 | 12/2008 | Pung et al. | |
| 2010/0239353 A1 * | 9/2010 | Prax | A45D 34/04 401/133 |
| 2018/0333566 A1 | 11/2018 | Follman et al. | |
| 2020/0214423 A1 | 7/2020 | Samangooie | |

FOREIGN PATENT DOCUMENTS

| | | |
|---|---|---|
| GB | 491053 A | 8/1938 |
| GB | 1562640 A | 3/1980 |
| WO | 2010101474 A1 | 9/2010 |

OTHER PUBLICATIONS

International Search Report for PCT/US2018/016374, International Filing Date Feb. 1, 2018, Date of completion of this opinion Mar. 25, 2018.

International Search Report for PCT/US2017/037066, International Filing Date Jun. 12, 2017, Date of completion of this international search Jul. 28, 2017.

Written Opinion of the ISA for PCTUS18/16374, International Filing Date Feb. 1, 2018, Date of completion of this opinion Mar. 25, 2018.

Written Opinion of the ISA for PCT/US2017/037066, International Filing Date Jun. 12, 2017, Date of completion of this opinion Jul. 28, 2017.

* cited by examiner

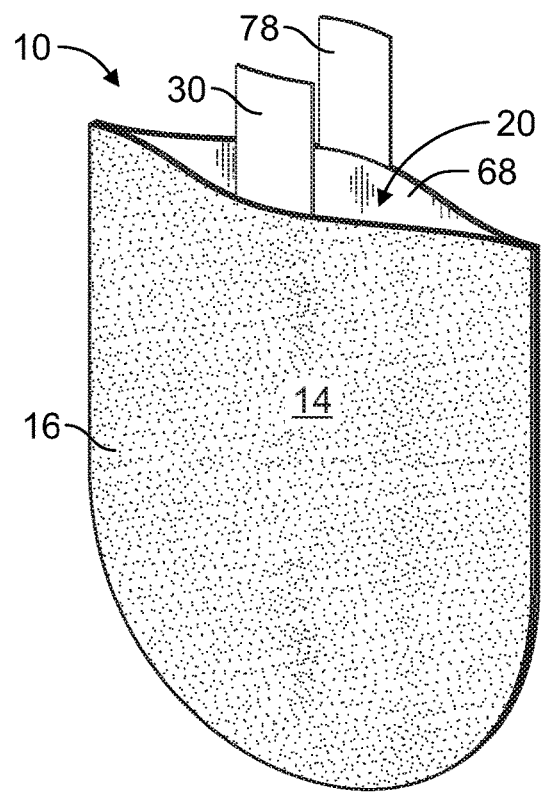
FIG. 36
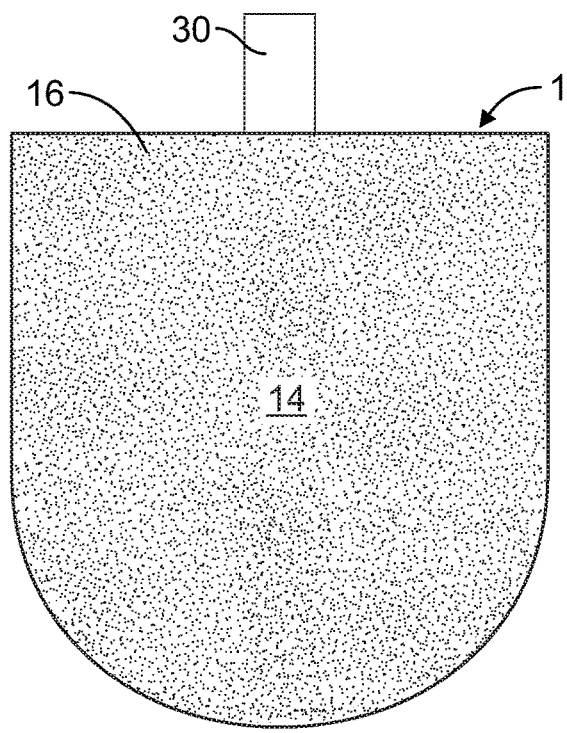 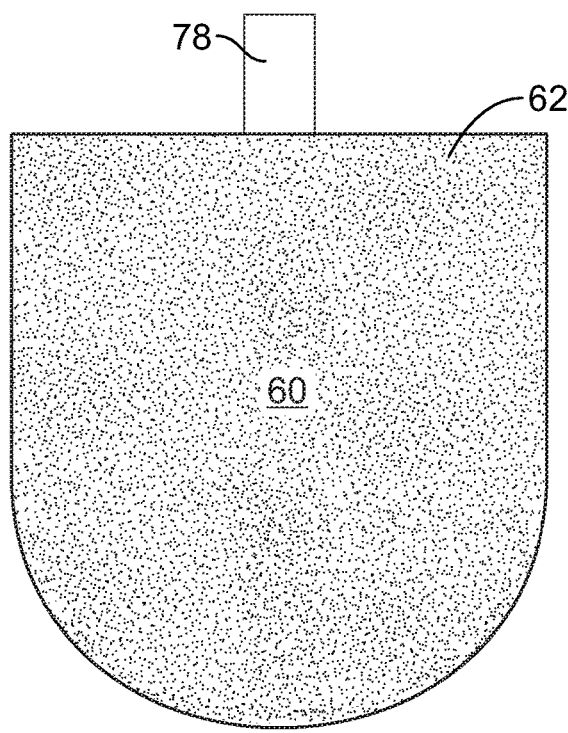
FIG. 37  FIG. 38

HAND-HELD APPLICATOR

FIELD OF THE INVENTION

The disclosed applicator relates to the field of hand-held liquid and cream applicators.

BACKGROUND

The application of a cream, polish, remover, repellant, or medicine usually requires the user to either place the substance from a container onto a cotton ball or swab or to place the substance directly on the surface it is being applied to. Doing so may result in too much of the substance being placed onto the surface or onto the cotton ball or swab. Further, such direct contact by the user may result in contamination of the substance or an adverse reaction if the substance contacts the skin or other organ of a user. A device that could eliminate possible contamination and adverse reactions would be useful in the application of such substances.

SUMMARY OF THE INVENTION

The present invention is a hand-held applicator for dispensing fill material in the nature of liquids or creams stored therein, the applicator comprising a first reservoir configured to store a first amount of the fill material, a first applicator layer adjacent the first reservoir and configured to dispense the first amount of fill material from the first reservoir, and a finger receiving space. The first reservoir comprises a reservoir access layer adjacent the first applicator surface and a back layer opposite the reservoir access layer. The reservoir access layer and back layer form a first fill space for receiving the fill material.

The reservoir access layer may comprise a first plurality of perforations configured to enable fluid communication between the first reservoir fill space and first applicator layer when the first plurality of perforations is in an open state. The reservoir access layer may also comprise a first hole transformable from a closed position covered by a tab to an open position wherein the tab is removed to expose the hole and enable fluid communication between the first reservoir fill space and the first applicator layer. The first applicator layer may be external facing, dispensing the fill material outside the applicator or internal facing, dispending the fill material into the finger-receiving space.

An applicator according the present invention may comprise a first and second applicator layer and first and second reservoir for storing and dispensing a first and second amount of fill material. The first and second amounts of fill material may be the same material or different material. The first and second applicator layers may be external facing, dispensing the fill material outside the applicator or internal facing, dispending the fill material into the finger-receiving space.

BRIEF DESCRIPTION OF THE DRAWINGS

FIG. 36 is an isometric view of a hand-held applicator according to the present invention;
FIG. 37 is a front elevation view of the hand-held applicator of FIG. 36;

FIG. 38 is a rear elevation view of the hand-held applicator of FIG. 36;

DETAILED DESCRIPTION OF THE DRAWINGS

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 5:
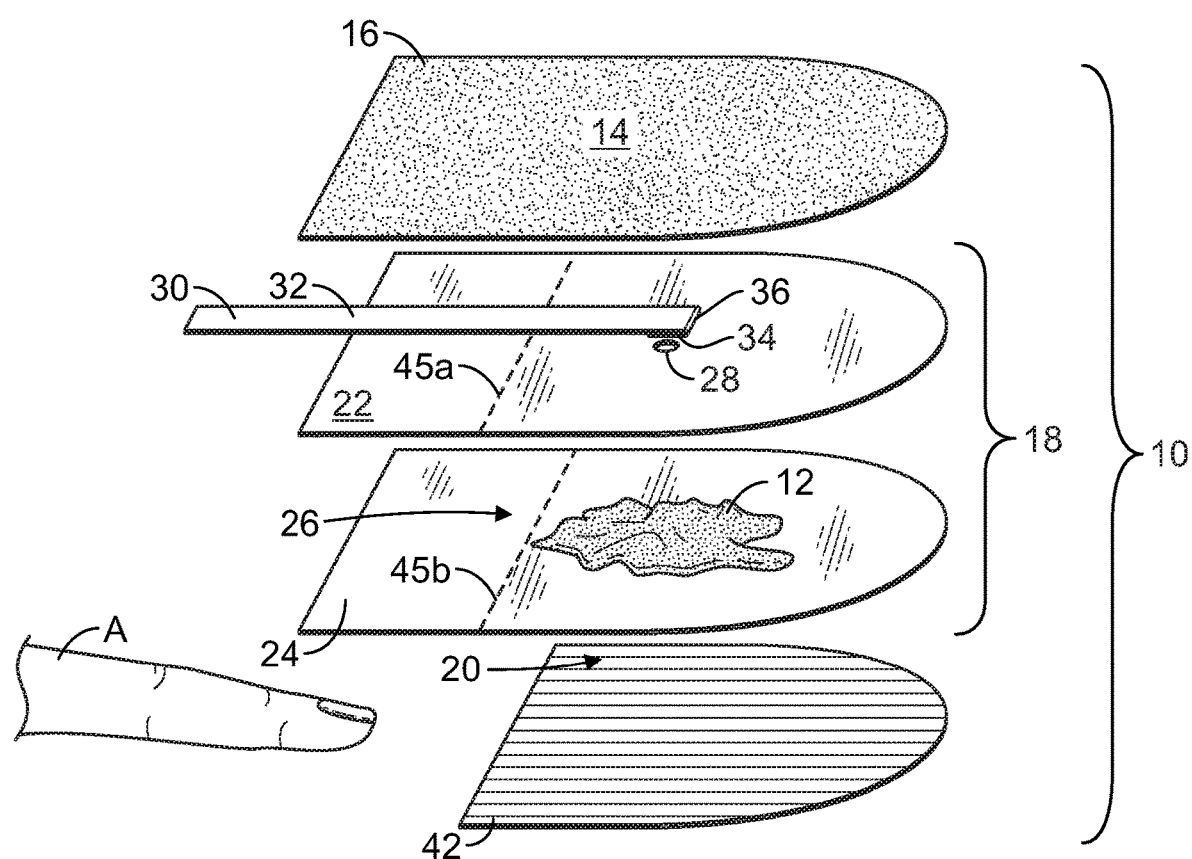
FIG. 5 is an exploded isometric view of the hand-held applicator of FIG. 1.

The drawings appended hereto show embodiments of an inventive, hand-held applicator 10 for storing and administering pre-determined amounts of fill material 12, including solutions, creams, polishes, medicines, medicaments, ointments and the like in a manner to minimize excess, waste, contamination, and mess. As represented in FIG. 5, an embodiment of the inventive hand-held applicator 10 generally comprises a first applicator layer 14 with an applicator surface 16, a first reservoir 18 adjacent the first applicator layer 14 and configured to store and dispense a predetermined amount of the fill material 12 through the first applicator layer 14, and a finger-receiving space 20 configured to receive a finger or fingers of the user or a similarly shaped extension of a tool or appliance.

The first applicator layer 14 in one embodiment may comprise a sponge or a foam (FIG. 5) and may comprise a cloth (FIG. 9) in another embodiment. The first applicator layer 14 is of various thickness, porosity, and composition depending on the specific fill material and application. For example, if a thicker cream is held in the reservoir layer an open-pore sponge or cloth would be preferable to enable ease of flow and transfer of the cream to the surface of the applicator. The sponge, foam, or cloth can be impregnated with product in crystalline or powder form and then activated upon introduction of liquid fill material 12 from the reservoir layer 18. The sponge, foam, or cloth applicator layers 14 are selected to be more or less abrasive depending on the specific application. When used, for example, to exfoliate skin and apply moisturizer the sponge or cloth is preferably more abrasive to improve its exfoliation efficacy. In contrast, when applying a cleaner to a headlight lens, a less abrasive sponge or cloth is desirable to avoid scratching the lens material.

The first reservoir 18 is formed from a reservoir access layer 22 and back layer 24 welded, glued, or sealed together around the periphery to form and define a fill space 26. The volume of the fill space is easily adjustable by sealing the fill space 26 at various points on the reservoir access layer 22 and back layer 24. A fill space seal 45a, 45b is shown in FIG. 5 to form a fill space of a first volume. Fill space seals 45a, 45b and 47a, 47b are shown in the embodiments of the applicator 10 seen in FIGS. 9, 10, 16, 18, and 19. The reservoir access layer 22 is adjacent the first applicator layer 14 and transformable between a first, closed position where the fill material is securely sealed in the first reservoir 18 and second, open position enabling fluid communication between the first reservoir 18 and first applicator layer 14 for dispensing the fill material 12. The materials selected to form the reservoir access layer 22 and back layer 24 will be dictated by the shelf life and/or nature of the fill material 12 and are generally selected from various foils or polyethylene films.

Figure 9:
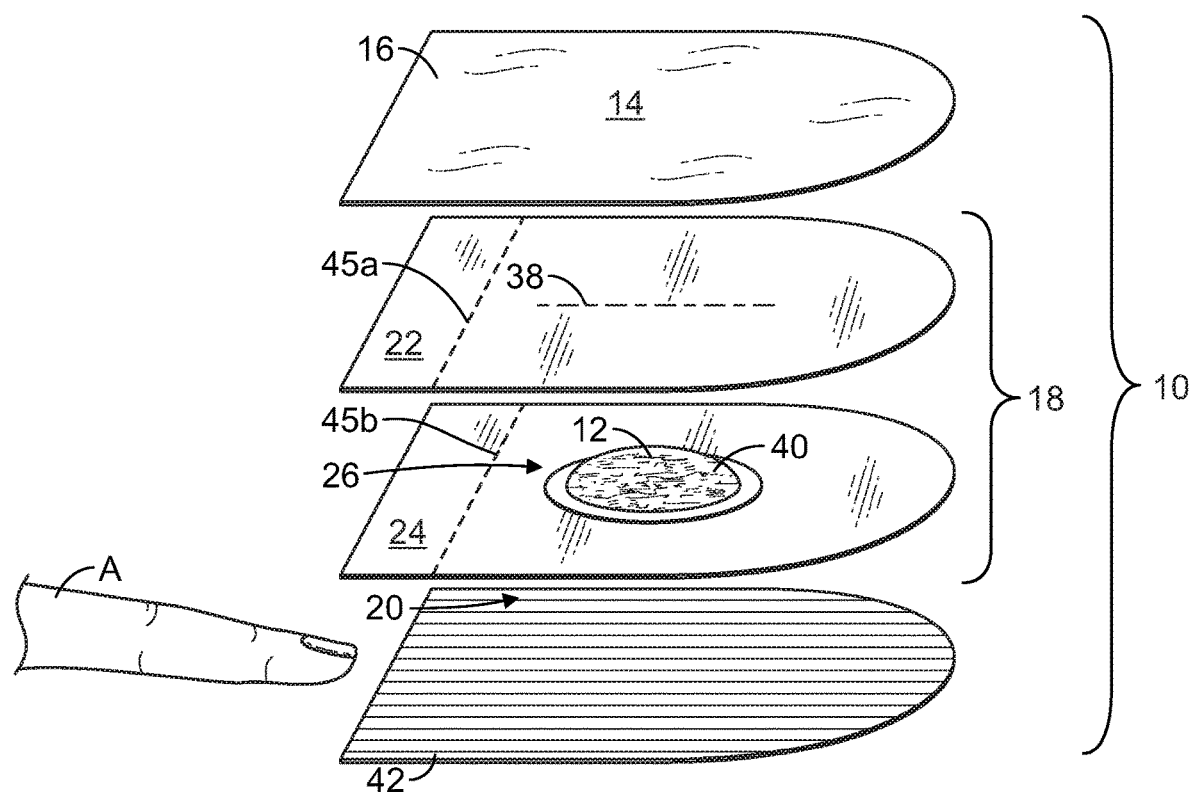
FIG. 9 is an exploded isometric view of the hand-held applicator of FIG. 6.

The reservoir access layer 22, as seen in the embodiments of the applicator 10 shown in FIGS. 5 and 9, is transformable from a first, closed position where the fill material 12 is secured within the fill space 26 and a second, open position enabling fluid communication between the first reservoir 18 and the first applicator layer 14. Referring to the embodiment of the applicator in FIG. 5, the first reservoir access layer 22 comprises an access hole 28 releasably covered by a first tab 30. The tab 30 comprises an extension portion 32 and a fold over portion 34 separated by a fold 36, with the fold over portion 34 affixed to the reservoir access layer 22 over the access hole 28. To maintain the structural integrity of the applicator 10 during operation, to expose the access hole 28 the user pulls on the extension portion 32 causing the tab 30 to unfurl or straighten the fold 36 as the fold over portion 34 releases from the reservoir access layer 22. This arrangement prevents unwanted pulling or distortion of the reservoir access layer 22.

As seen in the embodiment of the applicator 10 shown in FIG. 9, the reservoir access layer 22 may comprise a first plurality of perforations 38 that will open or burst when appropriate pressure is applied to the first reservoir 18. When first plurality of perforations 38 open, the reservoir access layer 22 facilitates fluid communication between the first reservoir 18 and first applicator layer 14.

Figure 10:
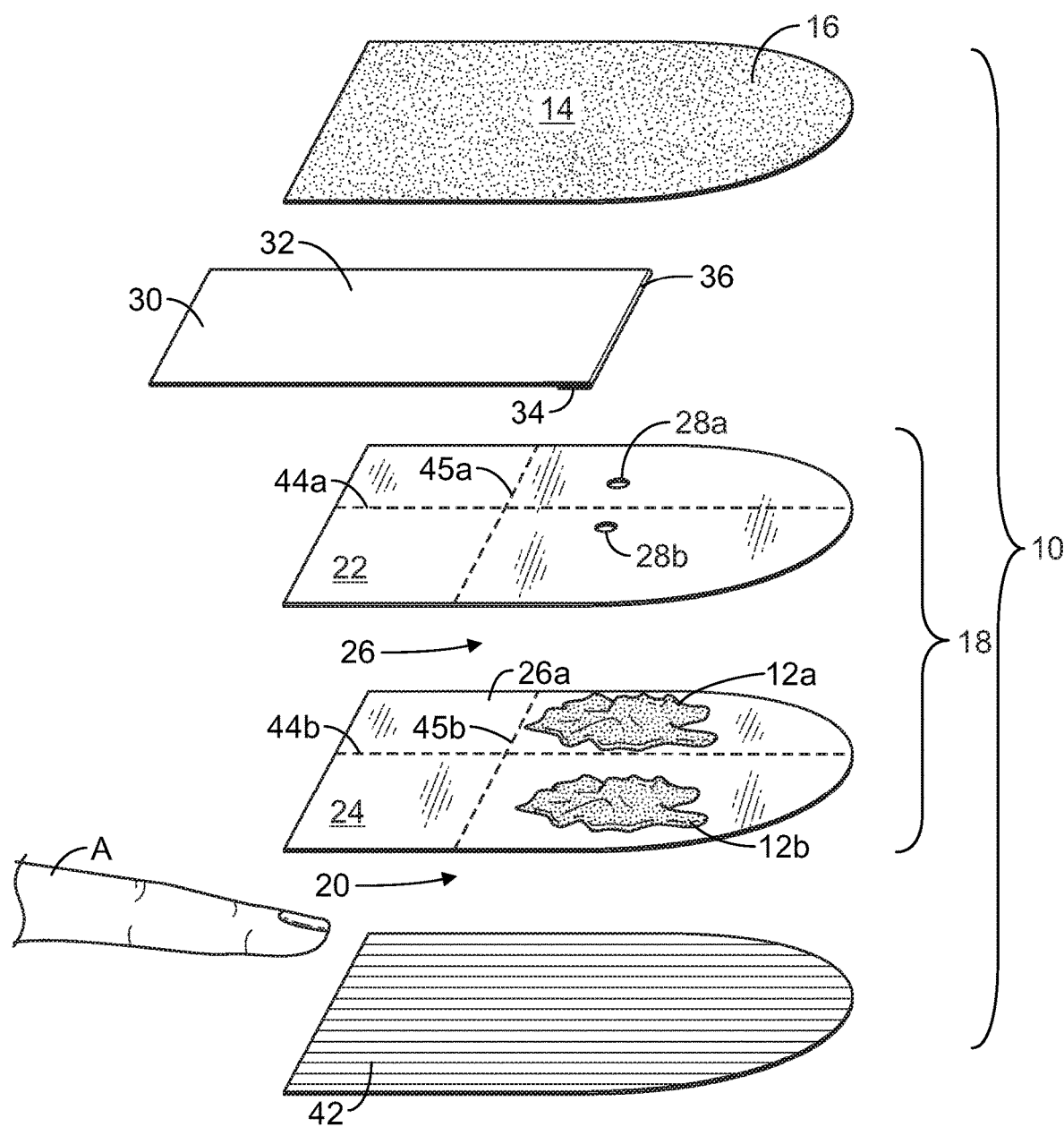
FIG. 10 is an exploded isometric view of a hand-held applicator according to the invention.
Figure 11:
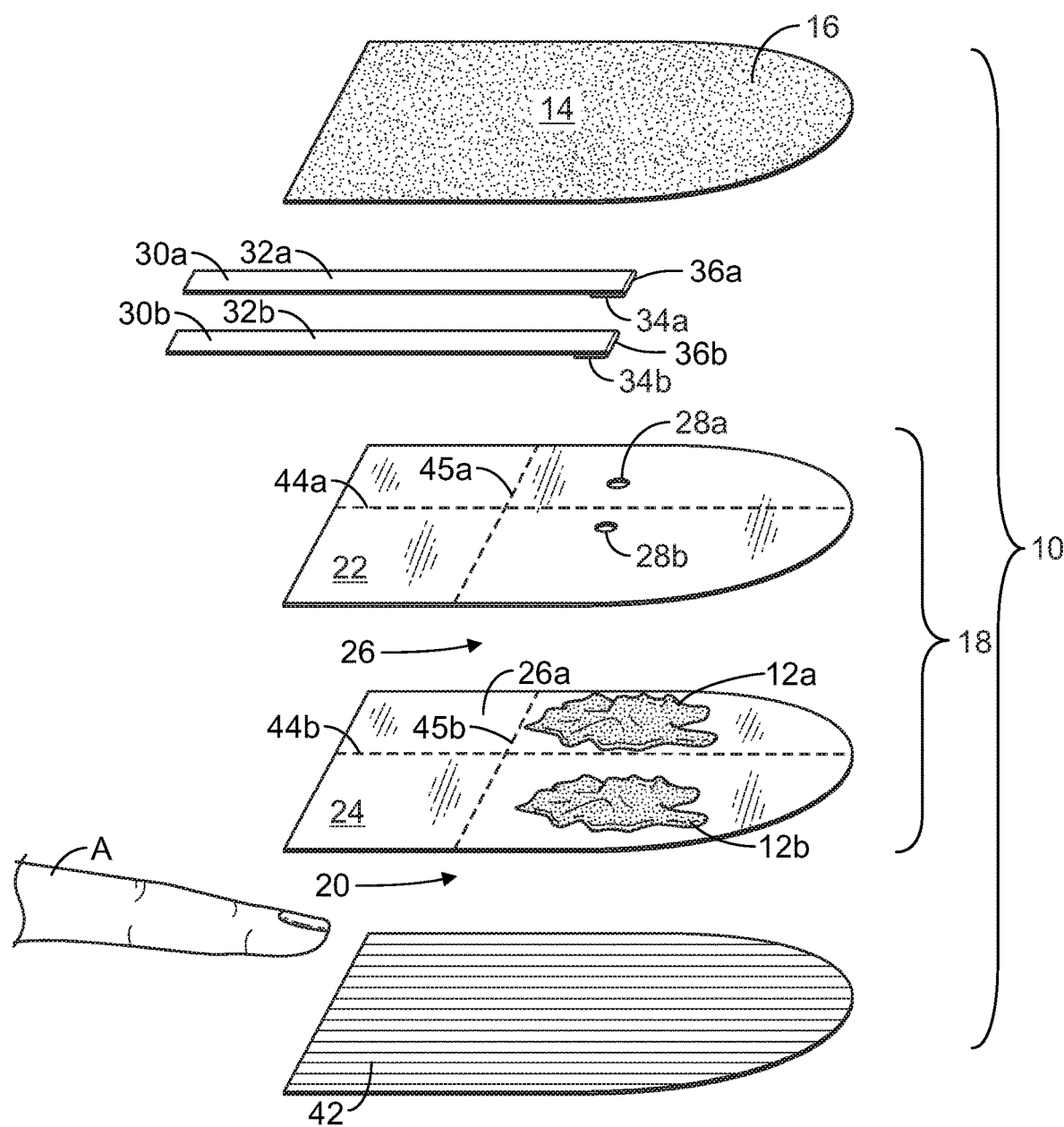
FIG. 11 is an exploded isometric view of a hand-held applicator according to the invention.
Figure 12:
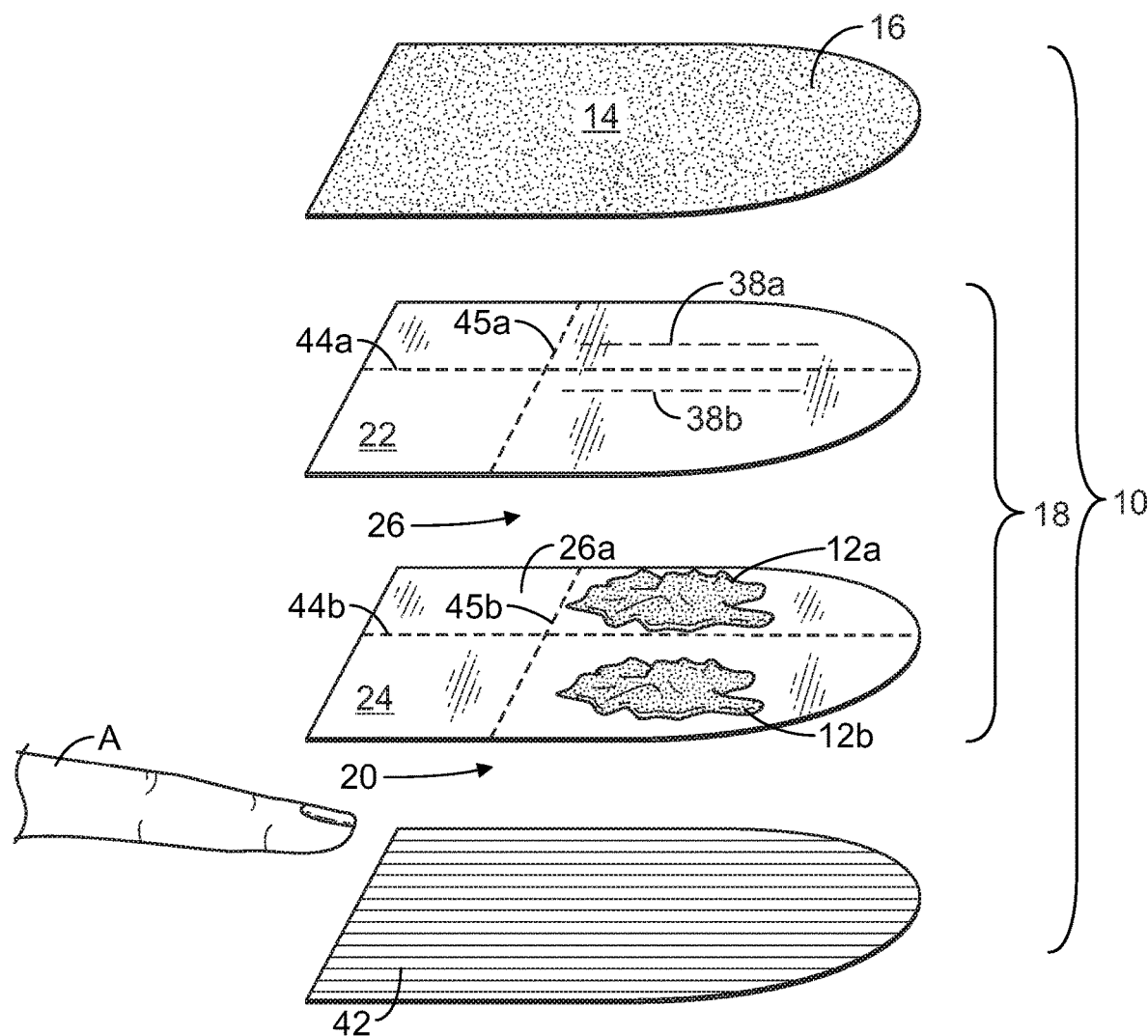
FIG. 12 is an exploded isometric view of a hand-held applicator according to the invention.

In other embodiments of the applicator 10 shown in FIGS. 10-12, the fill space 26 is further divided into a plurality of compartments. In these figures, the fill space 26 is divided into a first and a second compartment 26a, 26b and the fill material 12 is divided into a first material 12a and a second material 12b. The first and second materials 12a, 12b may be the same or different materials and may be the same or different quantities. The first and second compartments 26a, 26b can be formed by a weld or seal formed along guidelines shown as 44a, 44b in FIGS. 10-12, and shown as a completed weld or seal 44 in FIG. 13, on the reservoir access layer 22 and reservoir back layer 24. The fill space 26 divided into first and second compartment 26a, 26b at weld line 44a, 44b is exemplary and not limiting as to the number of compartments within the fill space.

FIG. 10 shows access holes 28a, 28b covered by a single tab 30. The tab 30 comprises an extension portion 32, fold over portion 34, and fold 36. When the first and second materials 12a, 12b are different or intended to be dispensed at different times, a first and second tab 30a, 30b, with first 32a and second 32b extension portions, as seen in FIG. 11, may be utilized. The applicator 10 of FIG. 12 uses a first and second plurality of perforations 38a, 38b to access the first and second materials 12a, 12b in the first and second compartments 26a, 26b of the fill space 26. In this configuration, the first plurality of perforations 38a is associated with and overlies the first compartment 26a of the fill space 26 and the second plurality of perforations 38b is associated with and overlie the second compartment 26b of the fill space 26.

The first reservoir 18 stores the fill material 12 to be dispensed by the first applicator layer 14. The fill material 12 to be dispensed may be applied directly in the fill space 18, as shown in the embodiment of the applicator in FIG. 5, or may be a capsule 40, as shown in the embodiment of the applicator in FIG. 9, or a plurality of capsules (not shown in the figures) placed into the fill space 26 and secured into position during assembly of the applicator 10. When the reservoir access layer 22 is in the access hole 26 and tab 30 configuration, shown in the embodiment of FIG. 5, and the fill material 12 is directly applied in the fill space 18, the fill material 12 is dispensed by removing the tab 30 and applying pressure to the fill material 12. The applied pressure urges the fill material 12 from the fill space 18, through the access hole 26, and to the first applicator layer 14 for application at the first applicator surface 16. The pressure is applied by the user at the finger or fingers in the finger-receiving space 20 and/or an additional finger or fingers outside the applicator 10 pinching or squeezing the first reservoir 18.

When the fill material 12 is stored in a material capsule 40, as shown in the embodiment in FIG. 9, the user should first burst the capsule to release the fill material 12 before removing tab 30 from the access hole 26. The pressure necessary to burst the material capsule 40 and release the fill material 12 is selected to be a reasonable pressure that can be easily applied by the user with a pinching action by the user's fingers, but greater than incidental pressure the applicator 10 may encounter during movement or storage. The bond strength of the weld or adhesive securing the tab 30 to the reservoir access layer over the access hole 26 and the tensile strength of the reservoir access layer should be greater than the burst pressure required to burst the material capsule 40. This prevents the user from applying a pressure to the material capsule 40 that will prematurely release the tab 30 from the reservoir access layer 22, exposing the access hole 26, and/or force the material capsule 40 through an open access hole 26.

In embodiments of the applicator 10 with a material capsule 40 and a reservoir access layer 22 comprising a first plurality of perforations 38, as shown in FIG. 9, the burst pressure required to burst the material capsule 40 and perforations 38 should be equal or the burst pressure required to burst the material capsule 40 should be less than the burst pressure required to open the perforations 38. This ensures the fill material 12 in the material capsule 40 will be released from the capsule at the same time or before the perforations 38 open.

Figure 1:
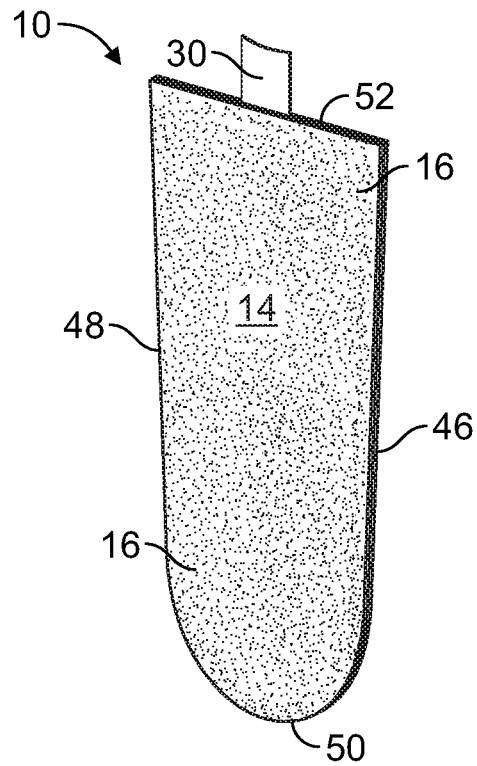
FIG. 1 is an isometric view of a hand-held applicator according to the invention.
Figure 2:
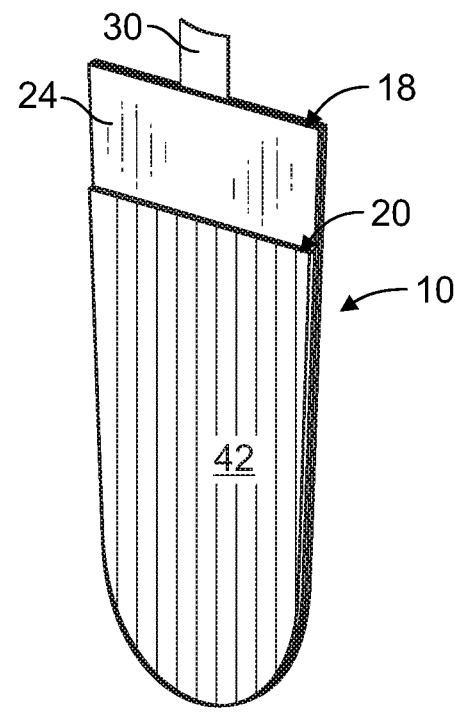
FIG. 2 is a second isometric view of the hand-held applicator of FIG. 1.
Figure 3:
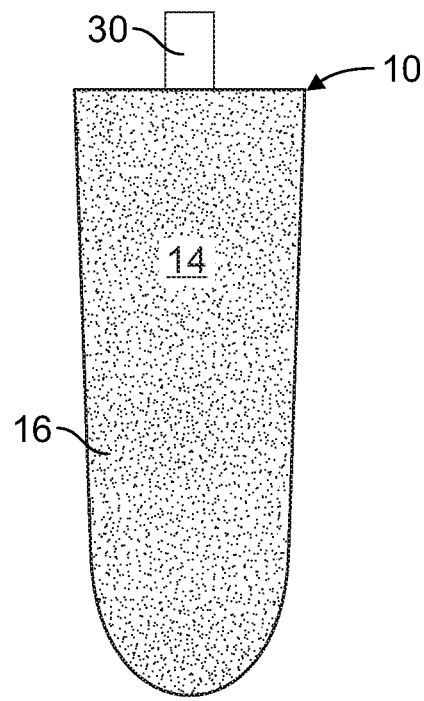
FIG. 3 is a front elevation view of the hand-held applicator of FIG. 1.
Figure 4:
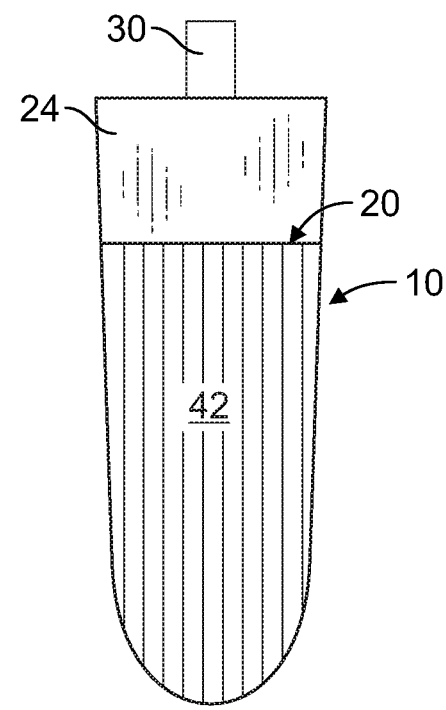
FIG. 4 is a rear elevation view of the hand-held applicator of FIG. 1.
Figure 6:
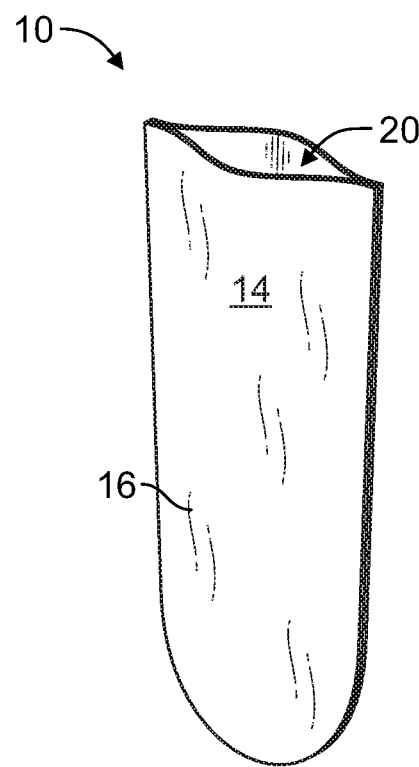
FIG. 6 is an isometric view of a hand-held applicator according to the invention.
Figure 8:
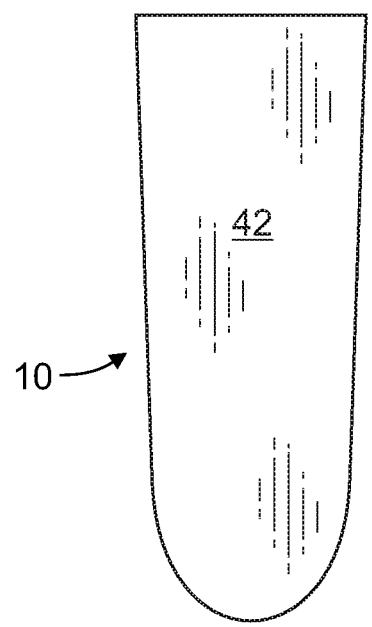
FIG. 8 is a rear elevation view of the hand-held applicator of FIG. 6.

As seen in the embodiments of the applicator 10 shown in FIGS. 2, 4, 5, 6 and 9, the finger receiving space 20 is formed by application of a film layer 42 to the back layer 24 of the first reservoir 18. The film layer 42 may extend less than the length of the first reservoir 18, as shown in FIGS. 2, 4, and 5, or may extend the entire length of the first reservoir 18, as shown in FIGS. 6, 8 and 9. The film layer 42 is composed of a readily deformable or elastic material enabling the film layer 42 to lay flat during storage of the applicator and expand to comfortably receive a finger during operation.

An embodiment of the applicator 10 according to the present invention is shown in FIGS. 1-4 wherein the applicator layer 14 comprises an external or outward-facing sponge or foam layer. This applicator 10 corresponds to the applicator 10 shown in exploded view in FIG. 5. The reservoir access layer 16 is the tab 24 and access hole 26 configuration and the finger receiving space 20 is formed by affixing a film layer 42 to the back layer 24 of the first reservoir 18. In this applicator 10, the finger receiving space 20 is dimensioned to receive a single finger, e.g., the index finger of the user. In this embodiment, the applicator layer 14 could also be cloth or the reservoir access layer 16 could incorporate first plurality of perforations instead of the tab and access hole.

Figure 13:
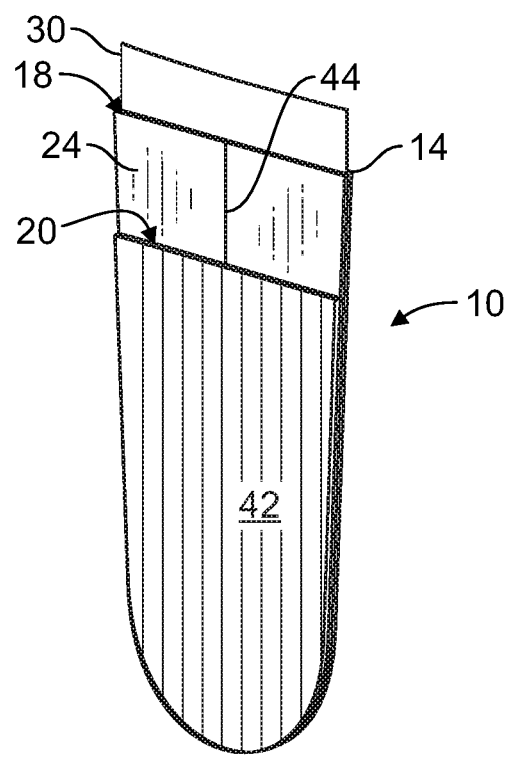
FIG. 13 is an isometric view of the hand-held applicator of FIG. 10.

FIGS. 10-13 show embodiments of an applicator 10 according to the present invention wherein the fill space 26 is divided into a plurality of compartments. The embodiment of the applicator 10 in FIGS. 10 and 13 utilizes a single tab 30 and removal of the tab 30 will expose both the first and second access holes 28a, 28b simultaneously. FIG. 10 shows the first and second amounts of the fill material 12a, 12b as being directly applied in the first and second compartments 26a, 26b of the fill space 26. A first and second material capsule, such as the material capsule 40 shown in FIG. 9, can also be utilized. The applicator 10 shown in FIG. 13 is the assembled applicator of FIG. 10 with the weld or seal guidelines 44a, 44b in FIG. 10 shown as a finished weld or seal 44.

The embodiments of the applicator 10 shown in FIGS. 11 and 12 will be assembled in similar manner to the applicator 10 shown in FIGS. 10, 13. The embodiment of the applicator 10 in FIG. 11 shows the fill space 26 comprising a first compartment 26a and a second compartment 26b, the first access hole 28a in the reservoir access layer 22 overlying the first compartment 26a and a second access hole 28b in the reservoir access layer 22 overlying the second compartment 26b. The first tab 30 releasably affixes to the first reservoir access layer 22 and overlies the first access hole 28a and a second tab 78 releasably affixes to the first reservoir access layer 22 and overlies the second access hole 28b.

In the embodiment of the applicator 10 shown in FIG. 12, the fill space 26 of the first reservoir 18 comprises a first compartment 26a and a second compartment 26b. A first plurality of perforations 38a in the reservoir access layer 22 overlies the first compartment 26a and a second plurality of perforations 38b in the reservoir access layer 22 overlies the second compartment 38b.

Figure 7:
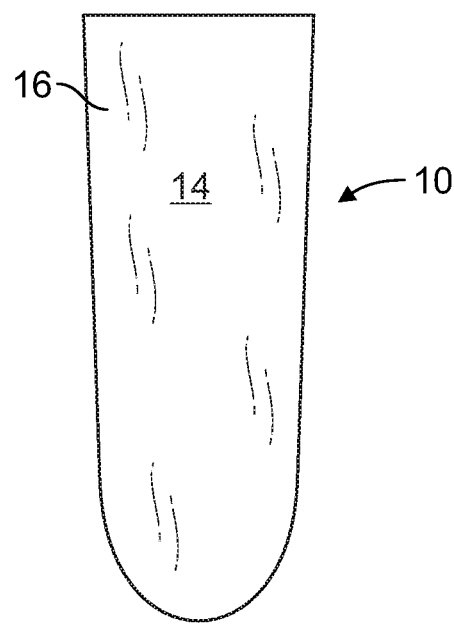
FIG. 7 is a second isometric view of the hand-held applicator of FIG. 6.

FIGS. 6-8, show another embodiment of applicator 10 according to the present invention wherein the applicator layer 14 comprises an external or outward-facing cloth layer. This applicator corresponds to the applicator 10 shown in exploded view in FIG. 9. The reservoir access layer (not shown FIGS. 6-8) is in the plurality of perforations configuration and the finger receiving space 20 is formed by affixing a film layer 42 to the back layer 24 of the first reservoir 18. As seen in FIG. 8, the film layer 42 extends the entire length of the first reservoir 18. The finger receiving space 20 is dimensioned to receive a single finger, e.g., the index finger of the user. In this embodiment, the applicator layer 14 could also be sponge or foam, or the reservoir access layer 16 could incorporate the tab and access hold configuration instead of the first plurality of perforations.

Figure 15:
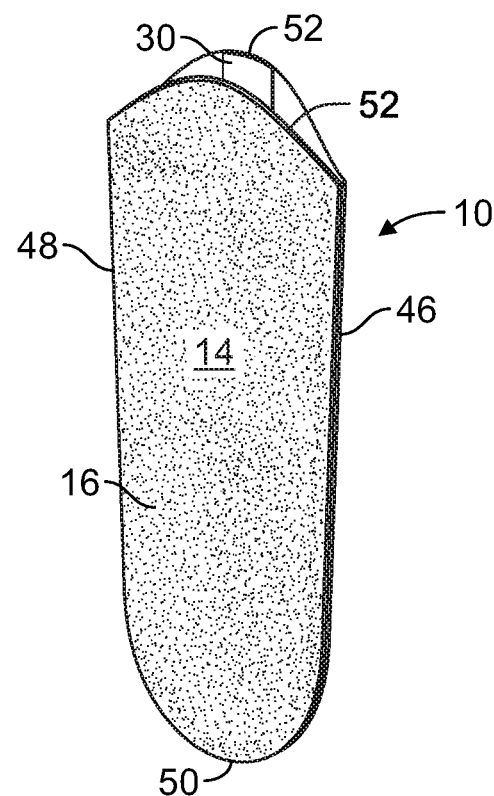
FIG. 15 is an isometric view of the hand-held applicator of FIG. 14.
Figure 14:
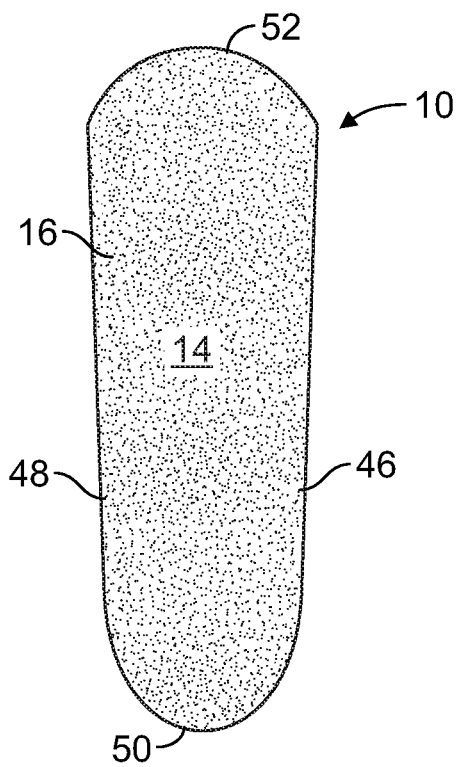
FIG. 14 is a front elevation view of a hand-held applicator according to the invention.

Returning to FIG. 1, the outer periphery of the applicator 10 is shown to generally comprise opposing, straight sides 46, 48, an arced bottom edge 50, and straight top edge 52, with the tab 30 extending above the top edge 52. To reduce or preclude occurrences of the tab 30 being inadvertently, prematurely pulled and dislodged from the reservoir access layer (not shown), the top edge 52 of the outermost layers of the applicator 10 can be arced or a radiused curve to extend over the tab 30 (see FIGS. 14, 15). The curvature at the top edge 52 can match or be different from the curvature at the bottom edge 50.

Figure 17:
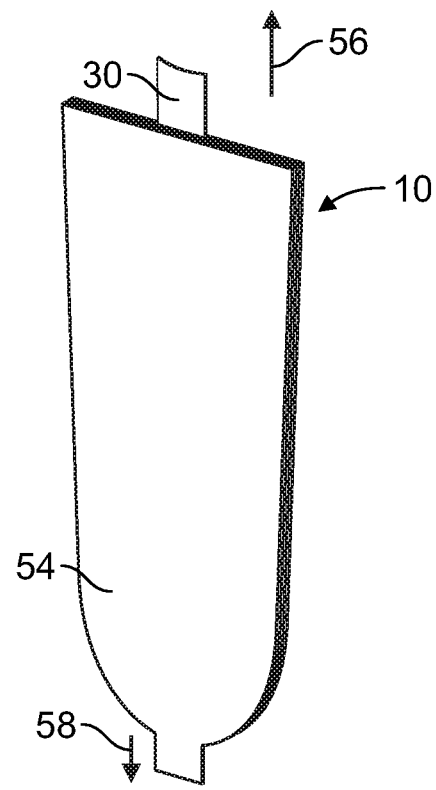
FIG. 17 is an isometric view of the hand-held applicator of FIG. 16.
Figure 16:
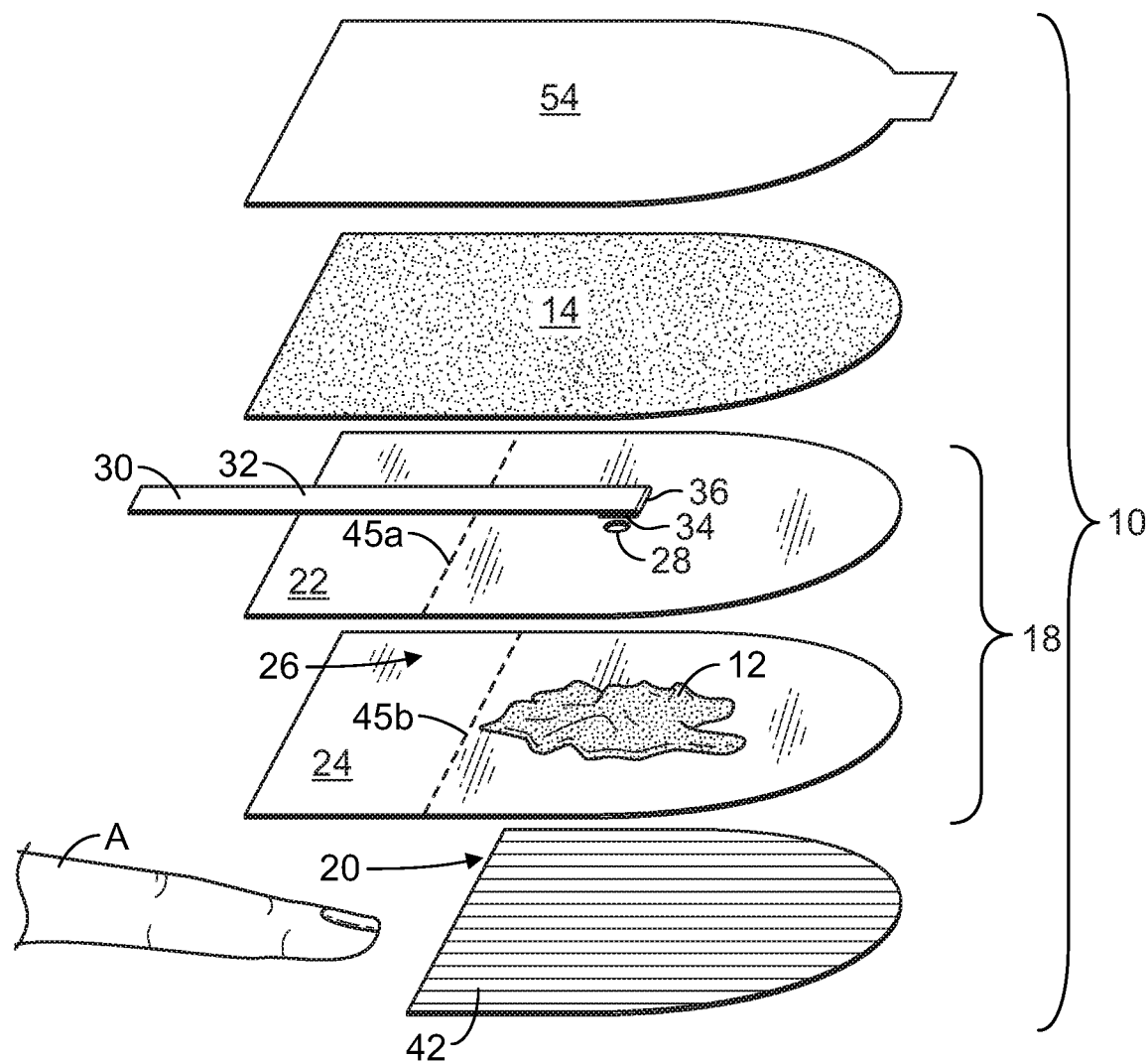
FIG. 16 is an exploded isometric view of a hand-held applicator according to the present invention.

Turning to FIGS. 16, 17, another embodiment of the applicator 10 according the present invention is shown having a protective covering 54 over the first applicator surface 16 to keep the first applicator surface clean and undamaged when not in use. As shown in FIG. 17, the tab 30 is removed from the applicator 10 pulling in the direction represented by arrow 56. The protective covering 54 is intended to be removed from the applicator in the direction represented by arrow 58. In this configuration, the likelihood of the protective covering 54 catching and pulling the tab 30 during removal of the protective covering 54 is reduced.

Applicators 10 described in connection with FIGS. 1-17 all generally comprise a single applicator layer 14 and a single reservoir 18. Other embodiments of the applicator 10 according to the present invention shown in FIGS. 18, 19 comprise multiple applicator layers 14, 60 and multiple reservoirs 18, 64. Referring first to the embodiment shown FIG. 18, the applicator 10 comprises a first applicator layer 14 having a first applicator surface 16, a first reservoir 18, a second applicator layer 60 having a second applicator surface 62, a second reservoir 64, and finger-receiving space between the first and second reservoirs 18, 64. As in previous applicators, the first reservoir comprises a reservoir access layer 22 and a back layer 24, with the reservoir access layer 22 and back layer 24 defining a fill space 26. The reservoir access layer 22 has a first plurality of perforations 38 enabling fluid communication between the fill space 26 of the first reservoir 18 and the first applicator layer 14.

This applicator 10 further comprises the second reservoir 64, the second reservoir 64 comprising a reservoir access layer 66 and back layer 68, together forming a fill space 70 for holding a second amount of fill material 72. The reservoir access layer 66 of the second reservoir 64 comprises a second plurality of perforations 72 enabling fluid communication between the fill space 70 and second applicator layer 60. In this applicator 10, the first and second applicator layers 14, 60 are cloth and first and second applicator surfaces 16, 62 extend outwardly or exteriorly. The first and second applicators layers 14, 60 can both be foam or sponge, or each applicator layer can be of different material. While the first and second amounts of fill material 12, 72 are shown directly applied into fill spaces 26, 70, either or both amounts of fill material 12, 72 could be contained in a material capsule, such as the material capsule 40 of FIG. 9. Likewise, while both reservoir access layers 22, 66 are shown to include a plurality of perforations 38, 74, one or both sets of perforations could be replaced by the tab 30 and access hole 28 configuration shown in FIG. 5.

Figure 18:
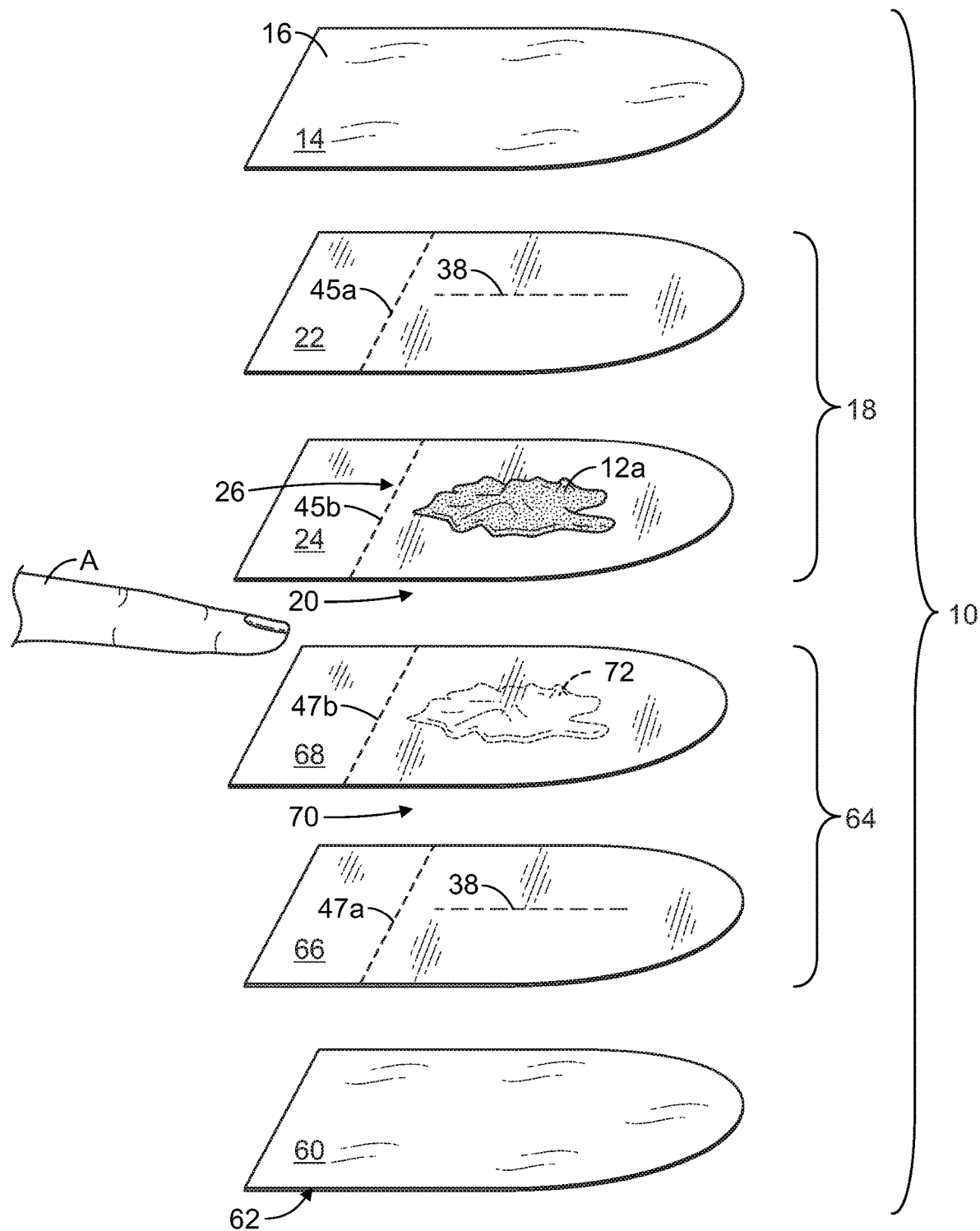
FIG. 18 is an exploded isometric view of a hand-held applicator according to the present invention.
Figure 19:
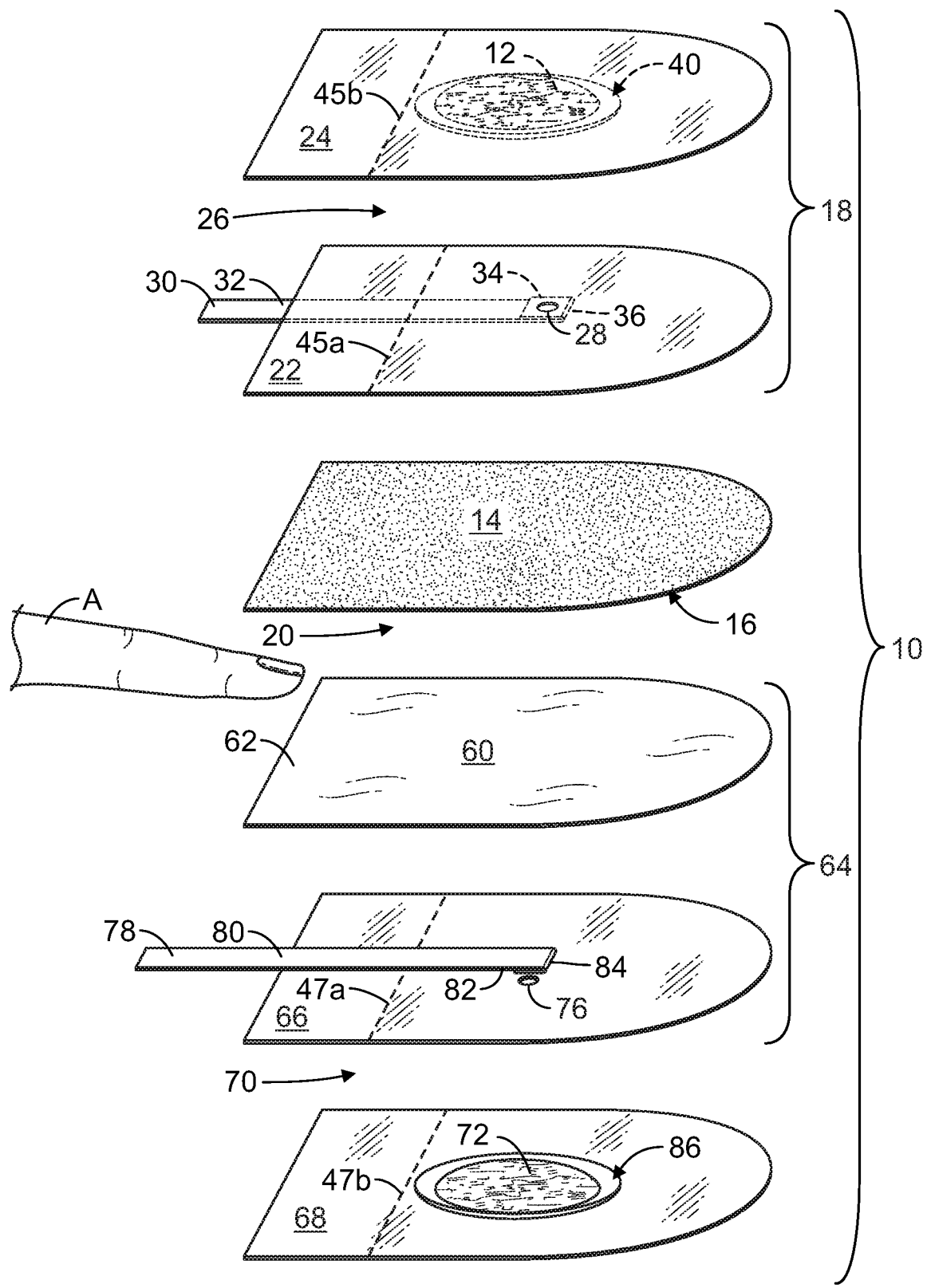
FIG. 19 is an exploded isometric view of a hand-held applicator according to the present invention.

In the embodiment of the applicator 10 seen in FIG. 19, the applicator 10 is shown having a first and a second applicator layer 14, 60 defining the finger-receiving space 20. The applicator surface 16 of the first applicator layer 16 faces inward and opposes the applicator surface 62 of the second applicator layer 60. In this configuration, the applicator surfaces 16, 62 will apply the fill material 12, 72 onto a finger in the finger-receiving space 20. Similar to the applicator described in FIG. 18, this applicator 10 comprises a first reservoir 18 adjacent to the first applicator layer 16, with a reservoir access layer 22 and back layer 24 defining a fill space 26 for receiving a first amount of the fill material 12.

The applicator 10 comprises a second reservoir 64 adjacent the second applicator layer 60, also with a reservoir access layer 66 and back layer 68 defining a fill space 70 for receiving a second amount of the fill material 72. Both reservoir access layers 22, 66 are in the tab 30, 78 and access hole 28, 76 configurations. The reservoir access layer 22 in the first reservoir 18 comprises the tab 30 with a tab extension 32, fold over portion 34, and fold 36. The reservoir access layer 66 in the second reservoir 64 comprises the tab 78 with a tab extension 80, fold over portion 82, and fold 84. The first applicator layer 14 is a sponge or foam layer while the second applicator layer 60 is a cloth. The applicator layers 14, 60 could be both sponge or foam, or both be cloth. In this applicator the fill material 12, 72 is contained in material capsules 40, 86 held within the fill spaces 26, 70 of the first and second reservoirs 18, 64. The fill material 12, 72 can also be applied directly into the fill spaces 26, 70, as seen in FIG. 18.

FIGS. 20-31 show assembled applicators 10 in multi-reservoir and multi-applicator layer embodiments similar to the applicators shown in FIGS. 18, 19. The embodiment of the applicator 10 shown FIGS. 20-22 comprise a first and second applicator layer 14, 60 of sponge or foam and outwardly facing applicator surfaces 16, 62. Pulling the first tab 30 will expose a first access hole and enable fill material from the first reservoir to be dispensed through the first applicator layer 16 and pulling the second tab 78 will, similarly, expose a second access hole and enable fill material from the second reservoir to be dispensed through the second applicator layer 60. The finger receiving space 20 is defined by the back surface of the first reservoir (not shown) and the back surface 68 of the second reservoir.

Figure 20:
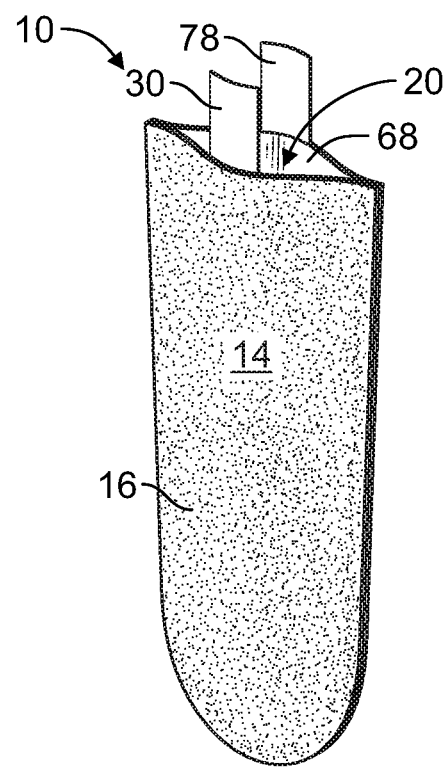
FIG. 20 is an isometric view of a hand-held applicator according to the present invention.
Figure 21:
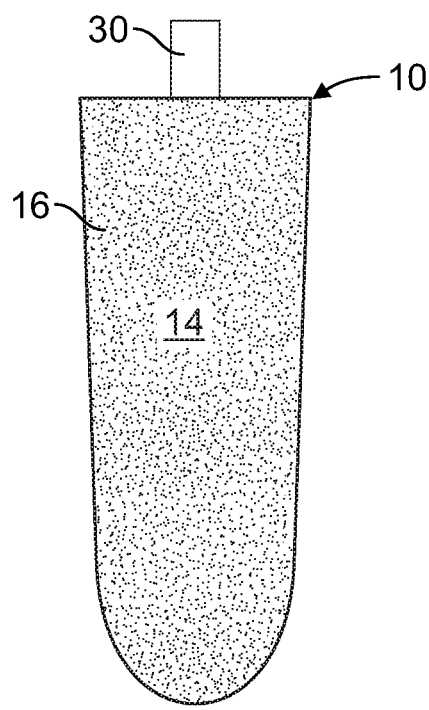
FIG. 21 is a front elevation view of the hand-held applicator of FIG. 20.
Figure 22:
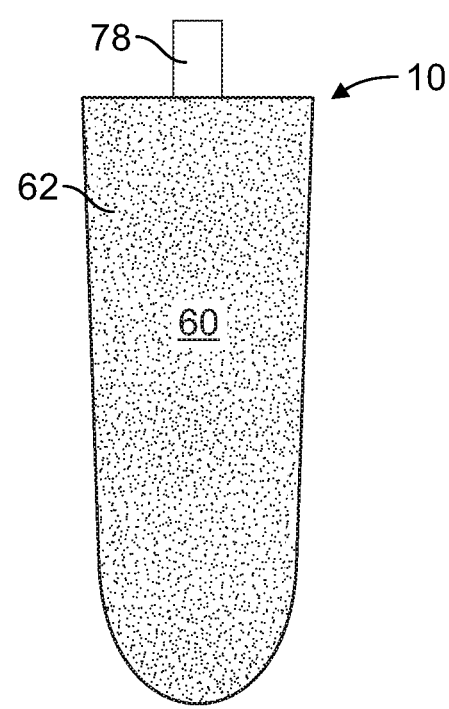
FIG. 22 is a rear elevation view of the hand-held applicator of FIG. 20.
Figure 23:
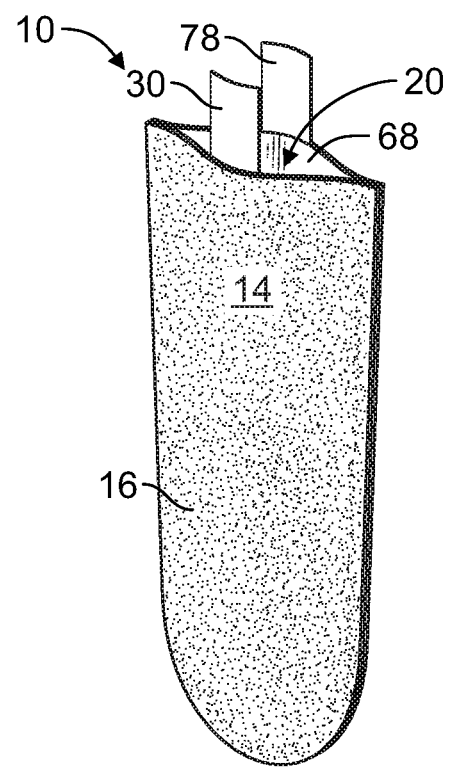
FIG. 23 is an isometric view of a hand-held applicator according to the present invention.
Figure 24:
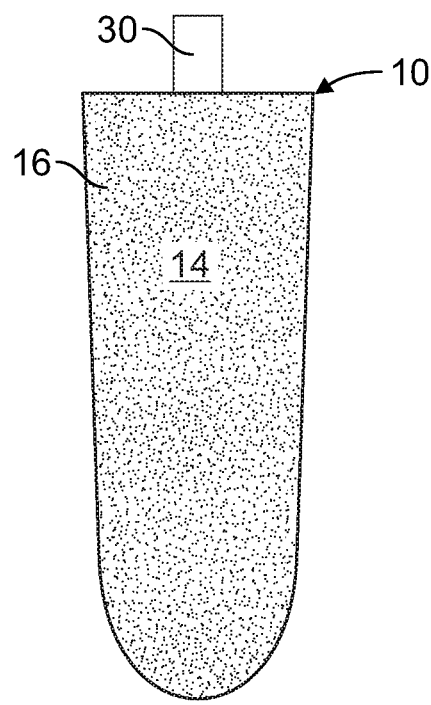
FIG. 24 is a front elevation view of the hand-held applicator of FIG. 23.
Figure 25:
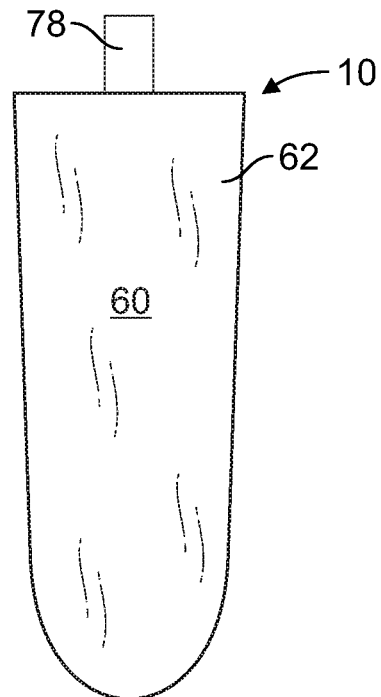
FIG. 25 is a rear elevation view of the hand-held applicator of FIG. 23.
Figure 26:
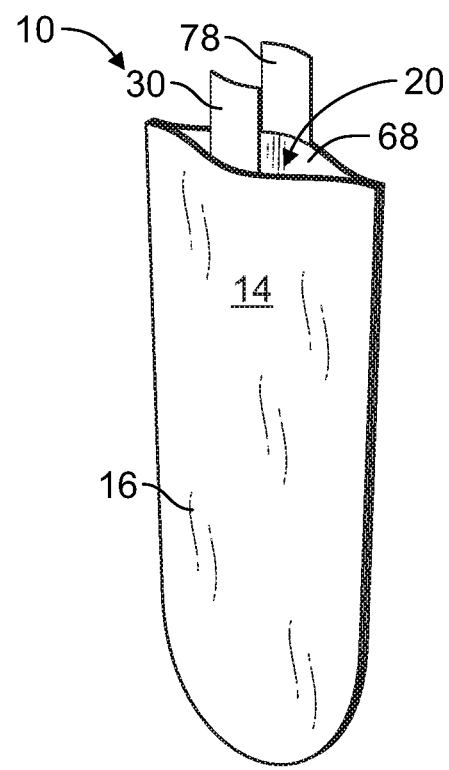
FIG. 26 is an isometric view of a hand-held applicator according to the present invention.
Figure 27:
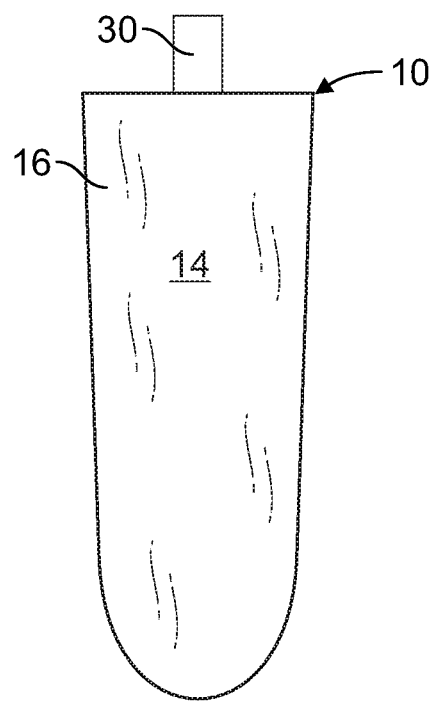
FIG. 27 is a front elevation view of the hand-held applicator of FIG. 26.
Figure 28:
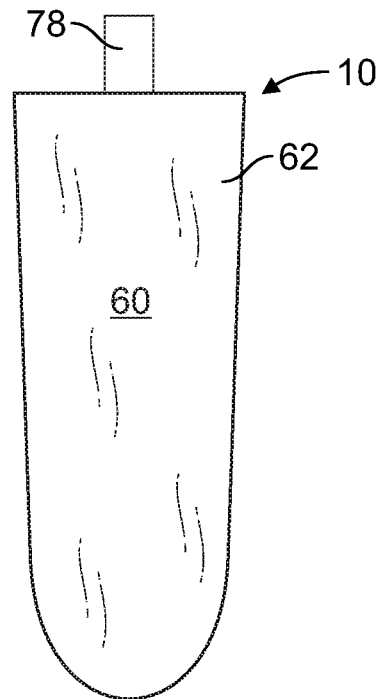
FIG. 28 is a rear elevation view of the hand-held applicator of FIG. 26.

Embodiments of the applicator 10 shown in FIGS. 23-25 and FIGS. 26-28 are identical in configuration to the applicator of FIGS. 20-22, but with various material combinations for the first and second applicator layers 14, 60 shown. In the embodiment of applicator 10 shown in FIGS. 23-25, the first applicator layer 14 is sponge or foam and the second applicator layer 60 is cloth. In the embodiment of applicator 10 shown in FIGS. 26-28, the first applicator layer 14 and second applicator layer 60 are both cloth.

Figure 29:
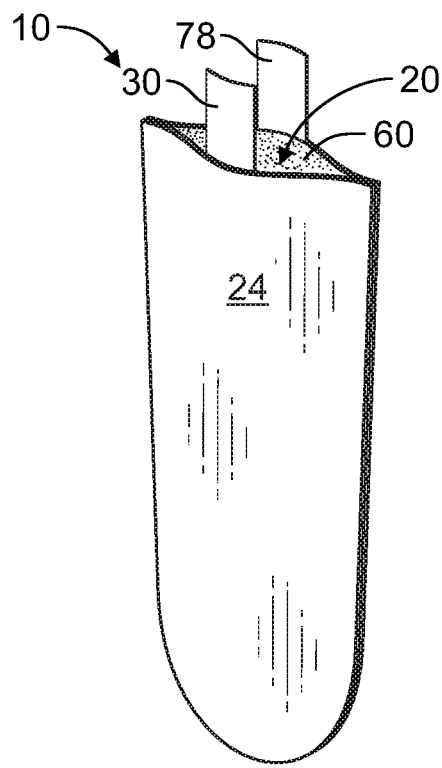
FIG. 29 is an isometric view of a hand-held applicator according to the present invention.
Figure 30:
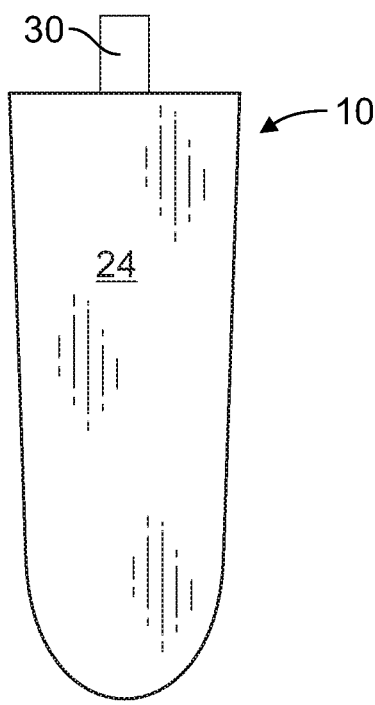
FIG. 30 is a front elevation view of the hand-held applicator of FIG. 29.
Figure 31:
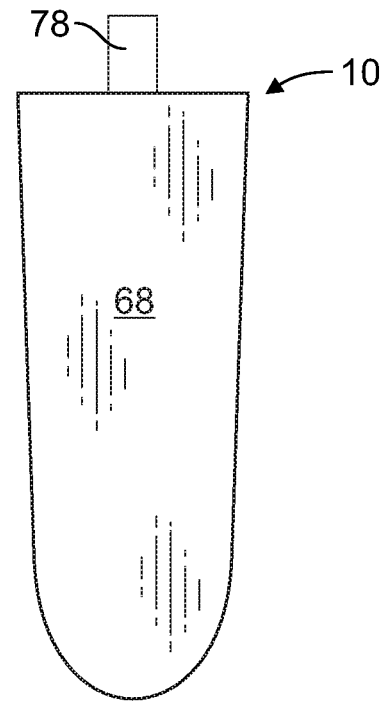
FIG. 31 is a rear elevation view of the hand-held applicator of FIG. 29.
Figure 32:
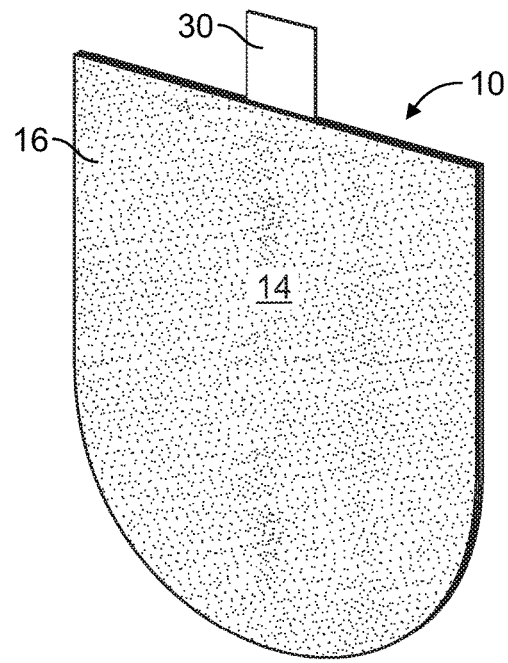
FIG. 32 is a front isometric view of a hand-held applicator according to the present invention.
Figure 33:
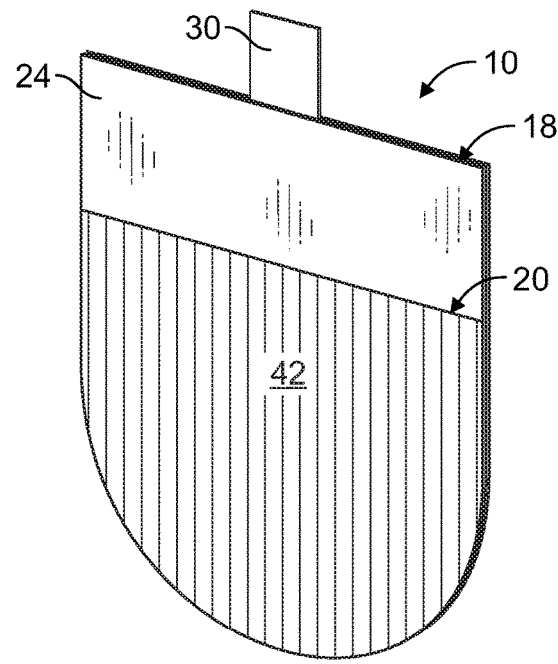
FIG. 33 is a rear isometric view of the hand-held applicator of FIG. 32.
Figure 34:
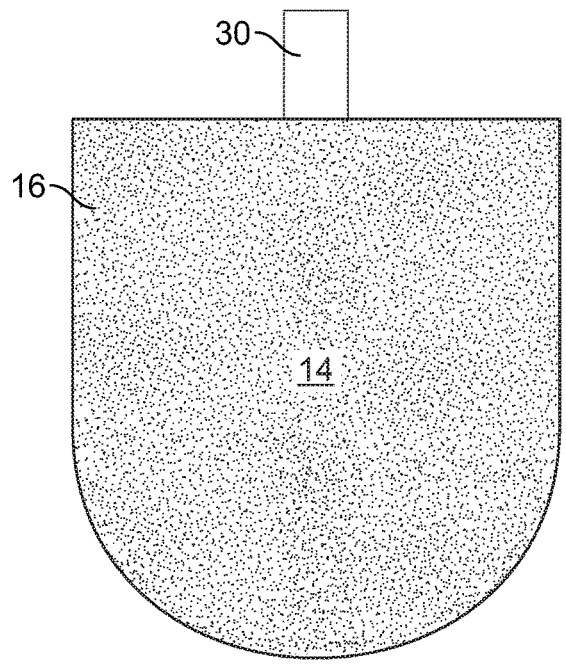
FIG. 34 is a front elevation view of the hand-held applicator of FIG. 20.
Figure 35:
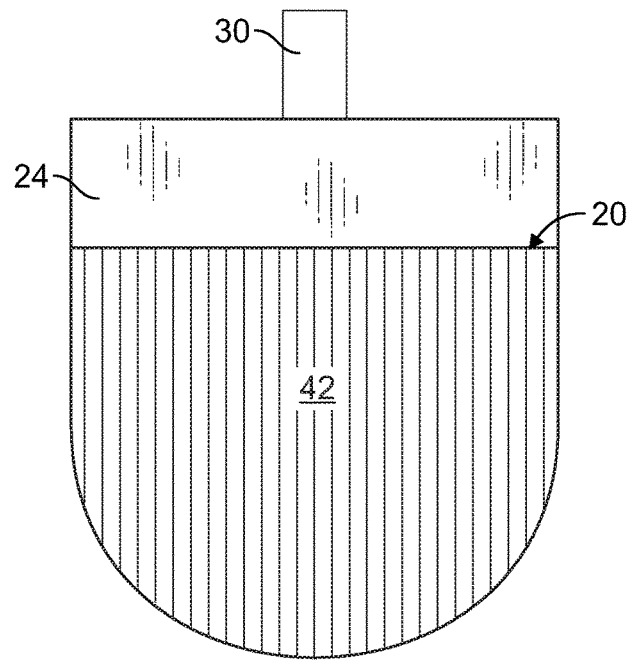
FIG. 35 is a rear elevation view of the hand-held applicator of FIG. 20.

The embodiment of the applicator 10 shown in FIGS. 29-31, is similar in configuration to the applicator 10 shown in the exploded view of FIG. 19 with internally facing first and second applicator layers (not shown), 60. In this applicator 10, the second applicator layer 60 is a sponge or foam. The first and second applicator layers 14, 60 can be either both sponge or foam, both be cloth, or be a combination of sponge or foam and cloth.

Figure 39:
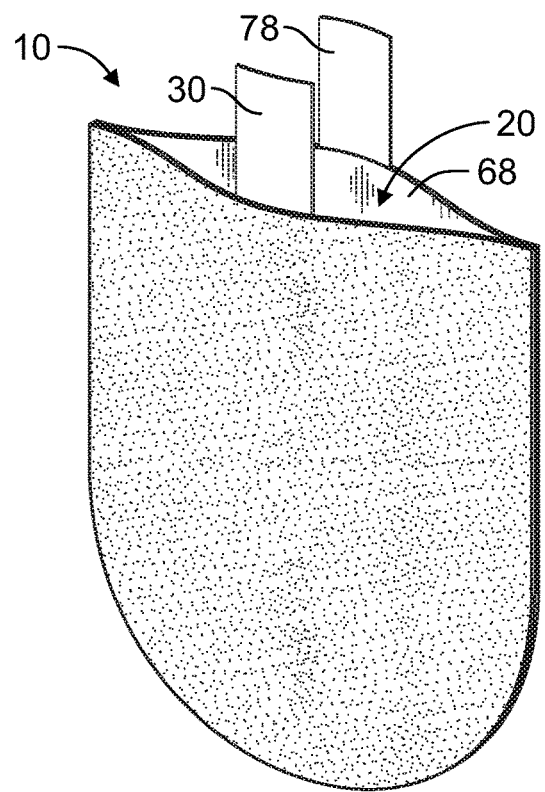
FIG. 39 is an isometric view of a hand-held applicator according to the present invention.
Figure 40:
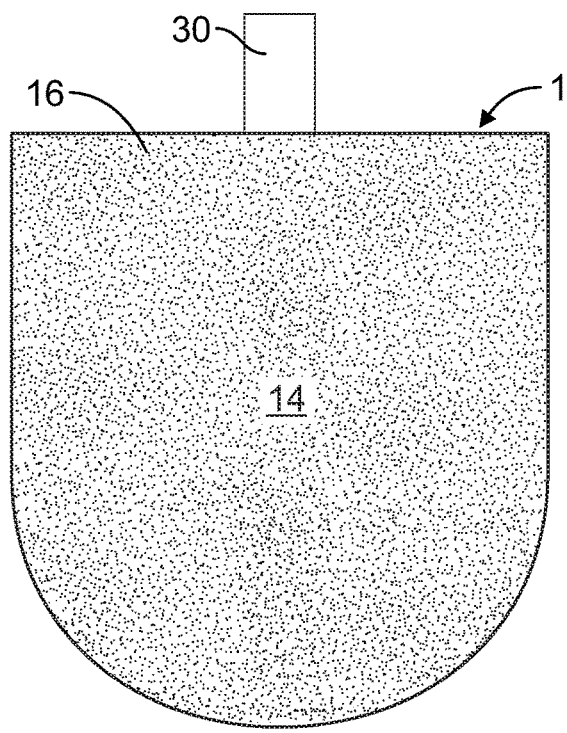
FIG. 40 is a front elevation view of the hand-held applicator of FIG. 39.
Figure 41:
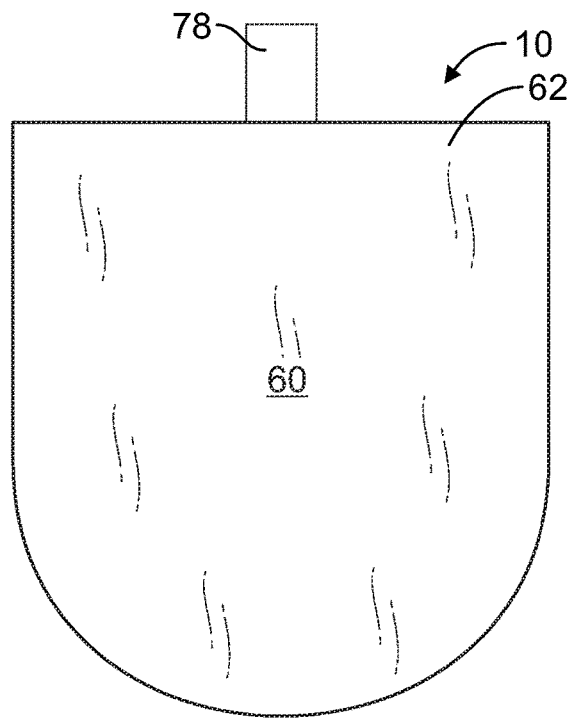
FIG. 41 is a rear elevation view of the hand-held applicator of FIG. 39.
Figure 42:
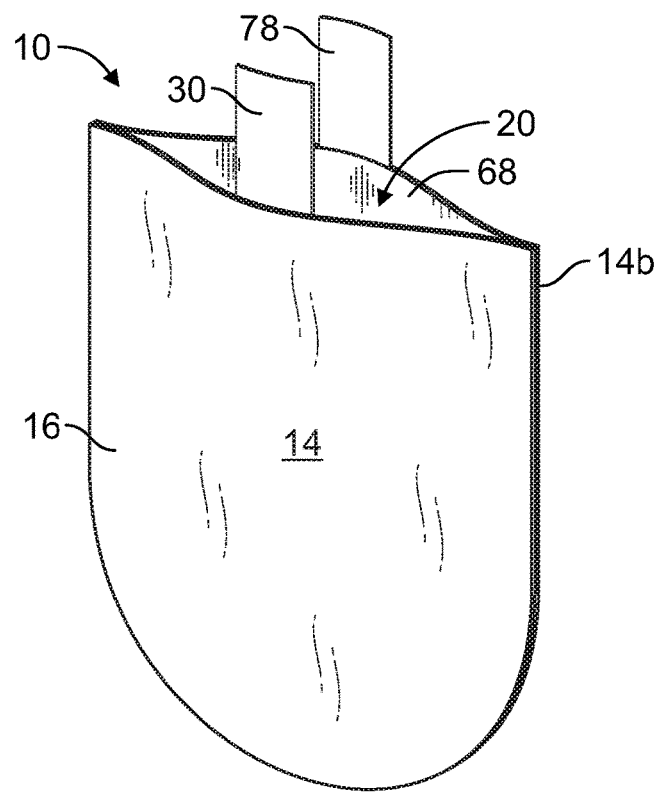
FIG. 42 is an isometric view of a hand-held applicator according to the present invention.
Figure 43:
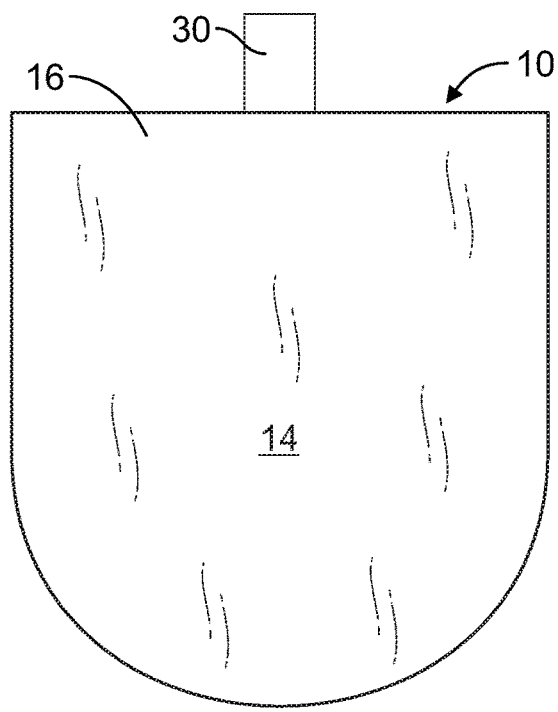
FIG. 43 is a front elevation view of the hand-held applicator of FIG. 42.
Figure 44:
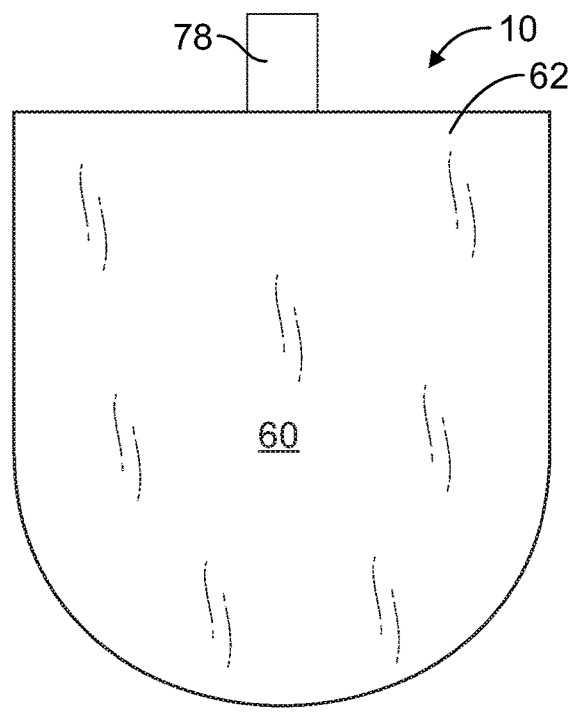
FIG. 44 is a rear elevation view of the hand-held applicator of FIG. 42.
Figure 45:
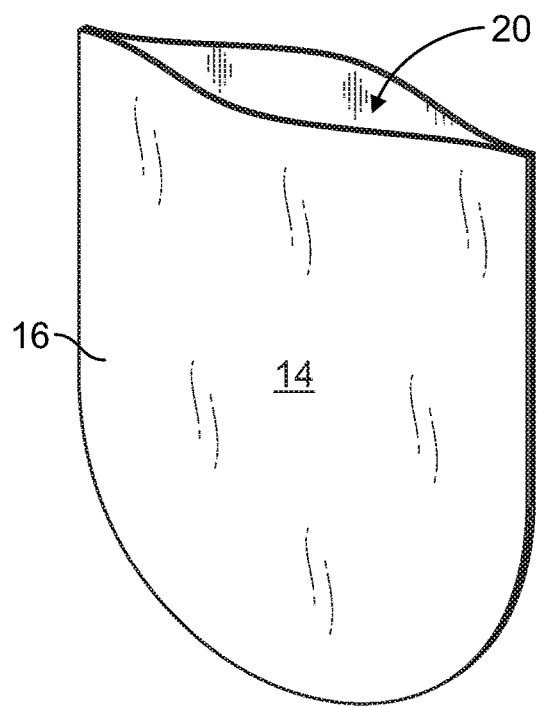
FIG. 45 is an isometric view of a hand-held applicator according to the present invention.
Figure 46:
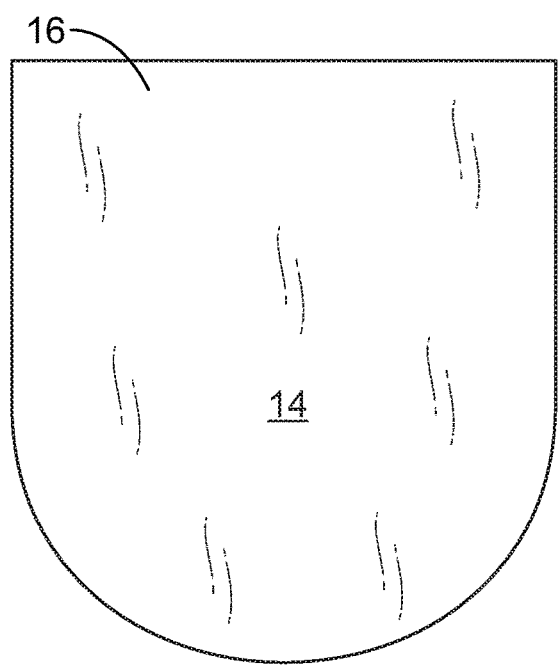
FIG. 46 is a front elevation view of the hand-held applicator of FIG. 45.
Figure 47:
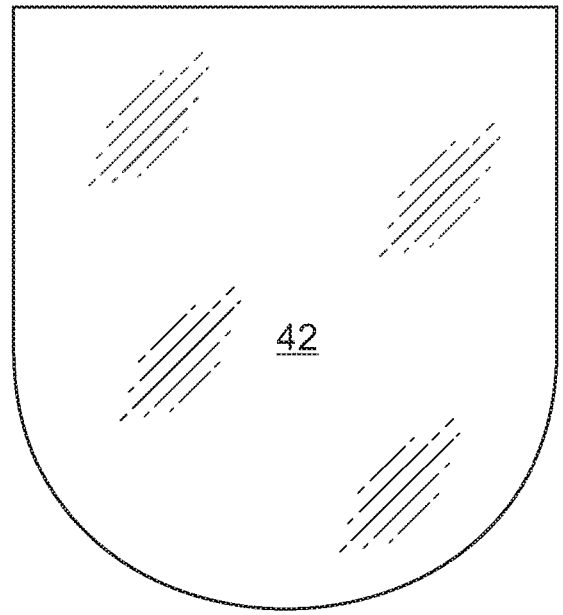
FIG. 47 is a rear elevation view of the hand-held applicator of FIG. 45.
Figure 48:
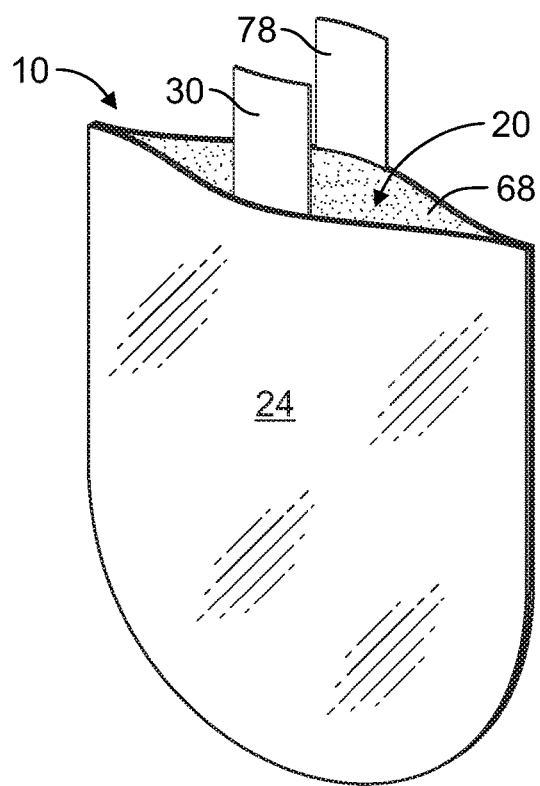
FIG. 48 is an isometric view of a hand-held applicator according to the present invention.
Figure 49:
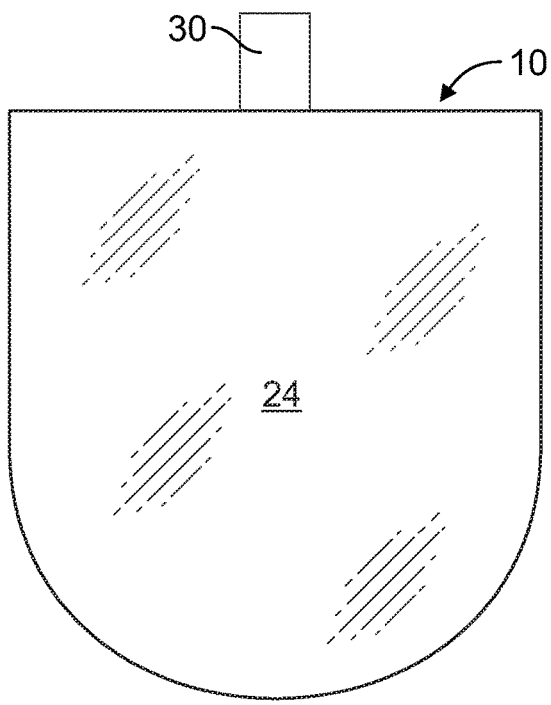
FIG. 49 is a front elevation view of the hand-held applicator of FIG. 48.
Figure 50:
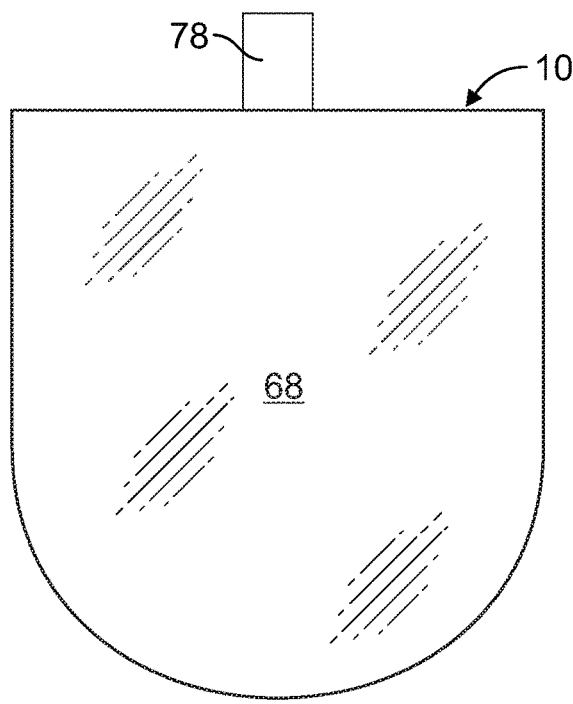
FIG. 50 is a rear elevation view of the hand-held applicator of FIG. 48.

The various embodiments of the applicator 10 described in connection with FIGS. 1-31, all include finger-receiving spaces 20 intended for single finger. The embodiments of the applicator 10 shown in FIGS. 32-49 all have finger-receiving spaces intended for two or more fingers. While the overall width of these applicators 10 is adjusted, as compared with the applicators shown in FIGS. 1-31, the overall structure, features, configuration, and functionality remain the same. Turning first to FIGS. 32-35, the embodiment of the applicator 10 shown in these figures is same as the applicator 10 shown in FIGS. 1-4, with the wider finger-receiving space 20. Reference numbers and the description of the applicator 10 of FIGS. 1-4 apply to the applicator 10 shown in FIGS. 32-35. Referring next to the embodiment of applicator 10 shown in FIGS. 36-38, the applicator 10 is the same as the applicator 10 shown in FIGS. 20-22, with the wider finger-receiving space 20. Reference numbers and the description of the applicator 10 of FIGS. 20-22 apply to the applicator 10 shown in FIGS. 36-38. The embodiment of the applicator 10 shown in FIGS. 39-41 is the same as the applicator 10 shown in FIGS. 23-25, with the wider finger-receiving space 20. Reference numbers and the description of the applicator 10 of FIGS. 23-25 apply to the applicator 10 shown in FIGS. 39-41. The embodiment of the applicator 10 shown in FIGS. 42-44 is the same as the applicator 10 shown in FIGS. 26-28, with the wider finger-receiving space 20. Reference numbers and the description of the applicator 10 of FIGS. 26-28 apply to the applicator 10 shown in FIGS. 42-44. The embodiment of the applicator 10 shown in FIGS. 45-47 is the same as the applicator 10 shown in FIGS. 6-8, with the wider finger-receiving space 20. Reference numbers and the description of the applicator 10 of FIGS. 6-8 apply to the applicator 10 shown in FIGS. 45-47. The embodiment of the applicator 10 shown in FIGS. 48-50 is the same as the applicator 10 shown in FIGS. 29-31, with the wider finger-receiving space 20. Reference numbers and the description of the applicator 10 of FIGS. 29-31 apply to the applicator 10 shown in FIGS. 48-50.

In one method of manufacture of the applicators shown in the appended figures and described herein, a vertical form, fill, and seal ("FFS") machine is utilized to affix the various layers of the device together and is then die cut to the desired final shape. A roll of film or films is set in the FFS machine. In the perforation embodiments, the roll of material maybe perforated during manufacturer or the micro perforations may be added as the material is unwinds from the roll. The film will go through forming stations to form the reservoir layer to hold the solutions or capsules with different solutions or saturated sponge/foam or cloth. In the process of forming and filling the reservoir layers, a roll of sponge/foam or cloth will follow the initial film roll/s as well as the elastic film to seal all components together. The assembly proceeds to the dye cutting station where it is cut to individual units of desired shape and size. In a horizontal form/fill/seal process, the roll of film with run through the forming station to form small or large reservoir layers in preparation for solutions or introduction of material capsules. A perforated film can then cover the solutions or capsules to seal the product close. A roll of cloth or sponge/foam will cover the filled pouch to be sealed. From there, the assembly will travel to the cutting/punching station to be cut in the desired shape. From there it will travel to cutting/punching stations to cut to desired shapes. In both methods, the perforated film can be replaced with a film having holes/apertures with a removable tab affixed over the holes.

Those skilled in the art will appreciate that the invention described herein is susceptible to variations and modifications other than those specifically described. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hand-held applicator for dispensing fill material stored in the applicator, the applicator comprising:
   (a) a first reservoir formed by a first reservoir access layer having a perimeter and affixed to a first back layer, the first reservoir access layer and first back layer defining a fill space configured to store a first amount of a fill material;
   (b) a first applicator layer adjacent and sealed to the first reservoir access layer and configured to dispense the first amount of the fill material;
   (c) a first tab releasably affixed to the first reservoir access layer and overlying and covering a first access hole the first tab is a separate piece from the first reservoir access layer, the first access hole transformable from a first, closed state covered by the first tab to a second, open state by applying a removal force to the first tab uncovering the first access hole and enabling fluid communication between the fill space of the first reservoir and the first applicator layer; and
   (d) a finger receiving space,
   wherein dislodging the first tab to expose the first access hole does not tear or damage the reservoir access layer.

2. The applicator of claim 1 wherein the fill space of the first reservoir comprises a first compartment and a second compartment, the first access hole in the reservoir access layer overlying the first compartment and a second access hole in the reservoir access layer overlying the second compartment, and the first tab releasably affixes to the first reservoir access layer and overlies the first access hole and the second access hole.

3. The applicator of claim 1 wherein the fill space comprises a first compartment and a second compartment, the first access hole in the reservoir access layer overlying the first compartment and a second access hole in the reservoir access layer overlying the second compartment, and wherein the first tab releasably affixes to the first reservoir access layer and overlies the first access hole and a second tab releasably affixes to the first reservoir access layer and overlies the second access hole.

4. The applicator of claim 1 wherein the tab comprises a tab extension portion and a fold over portion separated by a fold, the fold over portion releasably affixes the first reservoir access layer and overlies the first access hole, and wherein pulling on the tab extension in a tab removal direction causes the tab to unfurl and straighten at the fold.

5. The applicator of claim 1 wherein a first fill space of the first reservoir comprises a first and second compartment separated by a divider and wherein the fill material comprises an amount of a first material stored in and dispensed from the first compartment of the fill space and an amount of a second material stored in and dispensed from the second compartment of the fill space.

6. The applicator of claim 1 wherein the fill space of the first reservoir comprises a variable volume configured to store and dispense varying amounts of the fill material.

7. The applicator of claim 1 wherein the fill material is selected from the group consisting of a liquid, cream, polish, medicine, medicament, and ointment.

8. The applicator of claim 1 wherein the finger receiving space is adjacent the first reservoir and is formed by a film layer affixed to the first back layer of the first reservoir.

9. The applicator of claim 1 wherein the finger receiving space is formed adjacent an applicator surface of the first applicator layer by a film layer affixed to the first applicator layer, and the fill material from the first reservoir is dispensed through the reservoir access layer into the finger-receiving space.

10. The applicator of claim 1 wherein the first applicator layer is selected from the group consisting of a sponge, a cloth, and a foam.

11. The applicator of claim 1 further comprising:
(d) a second reservoir formed from a second reservoir access layer having a perimeter and affixed to a second back layer, the second reservoir access layer and second back layer defining a fill space configured to store a second amount of the fill material; and
a second applicator layer adjacent and sealed to the second reservoir access layer and configured to dispense the second amount of the fill material; and
(f) a second tab releasably affixed to the second reservoir access layer and overlying a second access hole, the second access hole transformable from a first, closed state covered by the second tab to a second, open state by applying a removal force to the second tab uncovering the second access hole and enabling fluid communication between the fill space of the second reservoir and the second applicator layer,
wherein dislodging the first tab to expose the second access hole does not tear or damage the second reservoir access layer.

12. The applicator of claim 11 wherein the fill space of the second reservoir comprises a first and second compartment separated by a divider and wherein the fill material comprises an amount of a first material stored in and dispensed from the first compartment of the fill space of the second reservoir and an amount of a second material stored in and dispensed from the second compartment of the fill space of the second reservoir.

13. The applicator of claim 11 wherein the first reservoir is adjacent the second reservoir and the finger-receiving space is formed between the first reservoir and second reservoir.

14. The applicator of claim 11 wherein the first applicator layer is adjacent the second applicator layer and the finger-receiving space is formed between the first applicator surface and the second applicator surface, wherein the fill material from the first reservoir is dispensed through the first reservoir access layer into the finger-receiving space and fill material from the second reservoir is dispensed through the second reservoir access layer into the finger-receiving space.

15. The applicator of claim 1 further comprising an outer periphery defined by a first and a second opposing side edge, a radiused bottom edge and a radiused top edge.

16. The applicator of claim 11 wherein the first fill space and second fill space each comprise a plurality of compartments.

17. The applicator claim 15 radiused top edge is identical to the radiused bottom edge or the radiused top edge is different than the radiused bottom edge.

18. The applicator of claim 1 further comprising an outer periphery defined by a first and a second opposing side edge, a radiused bottom edge and a radiused top edge and wherein the radiused top edge covers the tab.

19. The applicator of claim 1 wherein the first applicator layer comprises a first applicator surface, the first applicator surface is outwardly facing, and the applicator further comprises a protective covering releasably affixed to the first applicator surface.

20. The applicator of claim 1 wherein the fill material is selected from the group consisting of a liquid, cream, polish, medicine, medicament, and ointment.

21. The applicator of claim 1 wherein the first applicator layer is selected from the group consisting of a sponge, a cloth, and a foam.

22. An applicator for dispensing fill material stored in the applicator, the applicator comprising:
(a) a first reservoir configured to store a first amount of a fill material; the first reservoir formed from a first reservoir access layer and sealed to a first black layer
(b) a first applicator layer adjacent and affixed to_the first reservoir access layer and configured to dispense the first amount of the fill material; the first reservoir access layer having a first plurality of perforations transformable from a first, closed state to a second, open state by the first amount of the fill material applying a first burst force on the first plurality of perforations;
(c) a finger receiving space;
(d) a second reservoir configured to store a second amount of the fill material; the second reservoir formed from a second reservoir access layer and sealed to a second back layer; and
(e) a second applicator with an applicator surface, the second applicator adjacent_and affixed to the second reservoir access layer and configured to dispense the second amount of the fill material; the second reservoir access layer having a second plurality of perforations transformable from a first, closed state to a second, open state by the second amount of fill material applying a second burst force on the second plurality of perforations.

23. A hand-held applicator for dispensing fill material stored in the applicator, the applicator comprising:
(a) a first reservoir formed from a first reservoir access layer having a perimeter and sealed to a first back layer, the reservoir access layer and first back layer defining a fill space to store a first amount of a fill material;
(b) a first applicator layer adjacent and affixed to the first reservoir access layer having a first plurality of perforations transformable from a first, closed state to a second, open state by the fill material applying a first burst force on the plurality of perforations; and
(c) a finger receiving space,
wherein the first applicator layer in the second, open state enables fluid communication between the fill space of the first reservoir and the first applicator layer.

24. The applicator of claim 23 wherein the fill space of the first reservoir comprises a first and second compartment separated by a divider and wherein the fill material comprises an amount of a first material stored in and dispensed from the first compartment of the fill space and an amount of a second material stored in and dispensed from the second compartment of the fill space, wherein the first plurality of perforations in the first applicator layer overlies the first compartment and the first plurality of perforations in the open state enables fluid communication between the first compartment and the first applicator layer, and a second plurality of perforations in the first applicator layer overlies the second compartment, the second plurality of perforations transformable from a first, closed state to a second, open state by the fill material applying a second burst force on the second plurality of perforations, the second plurality of perforations in the open state enables fluid communication between the second compartment and the first application layer.

25. The applicator of claim 23 wherein a first fill space of the first reservoir comprises a variable volume configured to store and dispense varying amounts of the fill material.

26. The applicator of claim 23 wherein the finger receiving space is adjacent the first reservoir and is formed by a film layer affixed to the first back layer of the first reservoir.

27. The applicator of claim 23 wherein the finger receiving space is adjacent the applicator surface of the first applicator layer, is formed by a film layer affixed to an applicator surface of the first applicator layer, and the fill material from the first reservoir is dispensed through a reservoir access layer into the finger-receiving space.

28. The applicator of claim 23 further comprising:
(d) a second reservoir formed from a second reservoir access layer having a perimeter and sealed to a second back layer to define a fill space to store a second amount of the fill material;
(e) a second applicator layer adjacent and affixed to the second reservoir access layer having a second plurality of perforations transformable from a first, closed state to a second, open state by the fill material applying a second burst force on the second plurality of perforations.

29. The applicator of claim 28 wherein the second fill space of the second reservoir comprises a first and second compartment separated by a divider and wherein the fill material comprises an amount of a first material stored in and dispensed from the first compartment of the second fill space and an amount of a second material stored in and dispensed from the second compartment of the second fill space.

30. The applicator of claim 28 wherein the first reservoir is adjacent the second reservoir and the finger-receiving space is formed between the first reservoir and second reservoir.

31. The applicator of claim 28 wherein the first applicator layer is adjacent the second applicator layer and the finger-receiving space is formed therebetween, and wherein the fill material from the first reservoir is dispensed through the first reservoir access layer into the finger-receiving space and the fill material from the second reservoir is dispensed through the second reservoir access layer into the finger-receiving space.

32. The applicator of claim 21 radiused top edge is identical to the radiused bottom edge or the radiused top edge is different than the radiused bottom edge.

33. The applicator of claim 28 wherein the first burst force and second burst force are the same.

34. The applicator of claim 28 wherein the first burse force and second burst force are different.

35. The applicator of claim 23 further comprising an outer periphery defined by a first and a second opposing side edge, a radiused bottom edge and a radiused top edge.

36. An applicator for dispensing fill material stored in the applicator, the applicator comprising:
(a) a first reservoir configured to store a first amount of a fill material; the first reservoir formed from a first reservoir access layer and sealed to a first back layer;
(b) a first applicator layer adjacent and affixed to the first reservoir access layer and configured to dispense the first amount of the fill material; a first tab releasably affixed to the first reservoir access layer and overlying and covering a first access hole, and transformable from a first, closed state to a second, open state by applying a removal force to the first tab;
(c) a finger receiving space;
(d) a second reservoir configured to store a second amount of the fill material; the second reservoir formed from a second reservoir access layer and sealed to a second back layer; and
(e) a second applicator with an applicator surface, the second applicator adjacent and affixed to the second reservoir access layer and configured to dispense the second amount of the fill material.

37. The applicator of claim 36 wherein a second tab is releasably affixed to the second reservoir access layer and overlying and covering a second access hole, and transformable from a first, closed state to a second, open state by applying a removal force to the second tab.

* * * * *